United States Patent [19]
Holcomb

[11] Patent Number: 6,042,531
[45] Date of Patent: Mar. 28, 2000

[54] ELECTROMAGNETIC THERAPEUTIC TREATMENT DEVICE AND METHODS OF USING SAME

[76] Inventor: Robert R. Holcomb, 2100 Pierce Ave. Room 443, Nashville, Tenn. 37212

[21] Appl. No.: 08/665,830

[22] Filed: Jun. 19, 1996

Related U.S. Application Data

[60] Provisional application No. 60/000,317, Jun. 19, 1995, provisional application No. 60/000,300, Jun. 19, 1995, provisional application No. 60/000,299, Jun. 19, 1995, provisional application No. 60/000,318, Jun. 19, 1995, and provisional application No. 60/001,012, Jul. 10, 1995.

[51] Int. Cl.[7] .................................................... A61N 1/00
[52] U.S. Cl. .............................................. 600/13; 600/15
[58] Field of Search ........................................... 600/9–15

[56] References Cited

FOREIGN PATENT DOCUMENTS

| | | |
|---|---|---|
| 0081109 | 6/1983 | European Pat. Off. . |
| 3128263 | 2/1983 | Germany ................................. 600/13 |
| 3024175 | 12/1993 | WIPO ..................................... 600/15 |

Primary Examiner—John P. Lacyk
Attorney, Agent, or Firm—Garvey, Smith, Nehrbass & Doody, LLC

[57] ABSTRACT

A therapeutic electromagnetic treatment device adapted to interact with bodies of living organisms, including a method of treating a living organism with the device, the device including a plurality of electromagnetic bodies comprising a plurality of magnetic poles substantially in a single plane; the magnetic bodies being oriented to define the four vertices of a quadrilateral shape, and each of the magnetic poles exerting a magnetic force on the other plurality of magnetic poles when the poles are electrically charged; a ferroconductor flux return ring secured to at least one of the poles turned away from the organism being treated; a ferromagnetic focusing ring containing a ferroconductor metal ring and an electromagnet of the same polarity as the pole attached to the focusing ring in proximity to the four poles of the quadrilateral shape; containment component for holding the magnetic poles of the magnetic bodies in the orientation; and power supply for magnetically energizing the electromagnetic bodies, the energized electromagnetic bodies, each generating a magnetic flub field, the four magnetic poles when energized together generate flux field with a sharp three dimensional gradient and comprises a flux generator head.

30 Claims, 9 Drawing Sheets

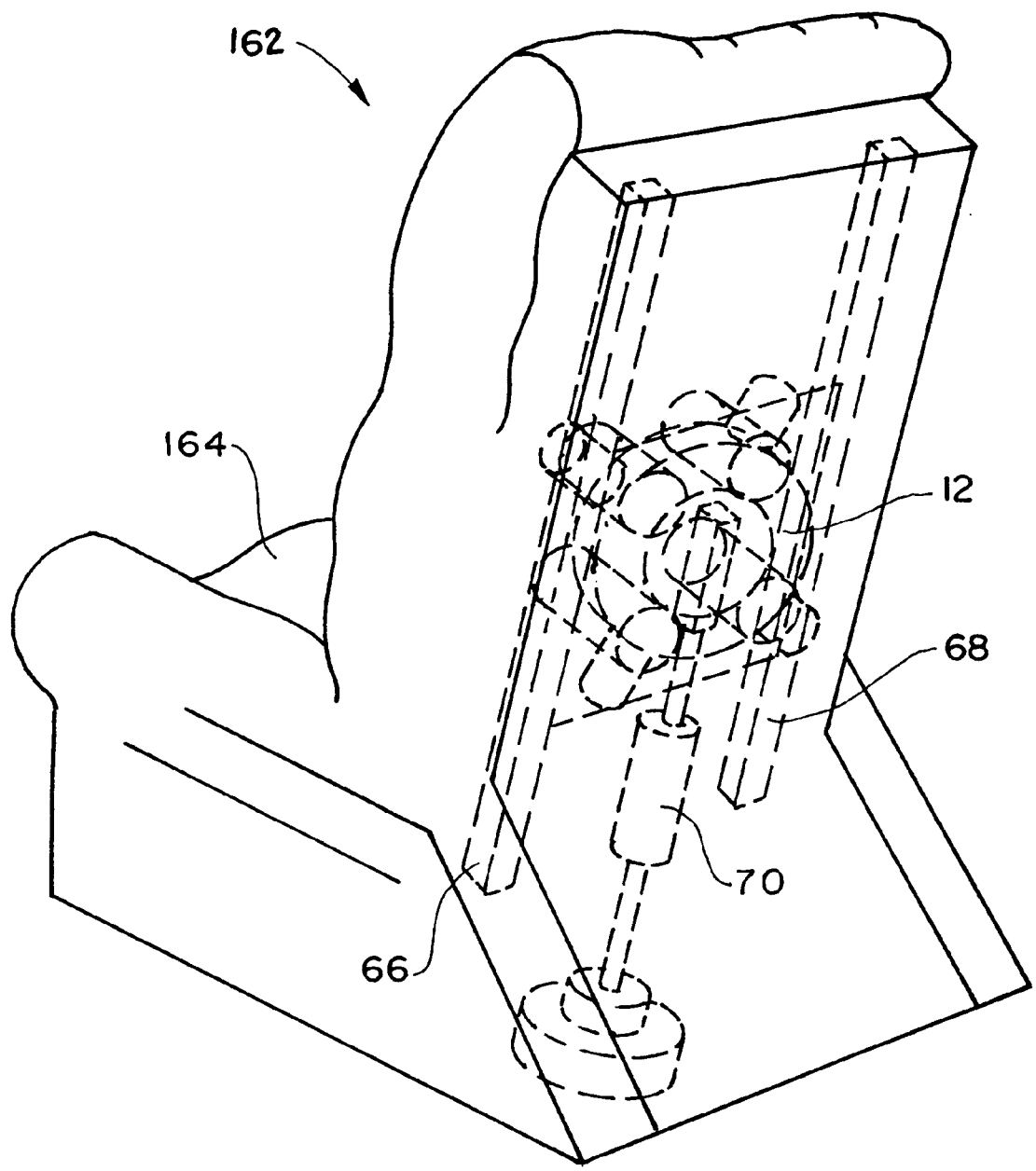
F I G. 6

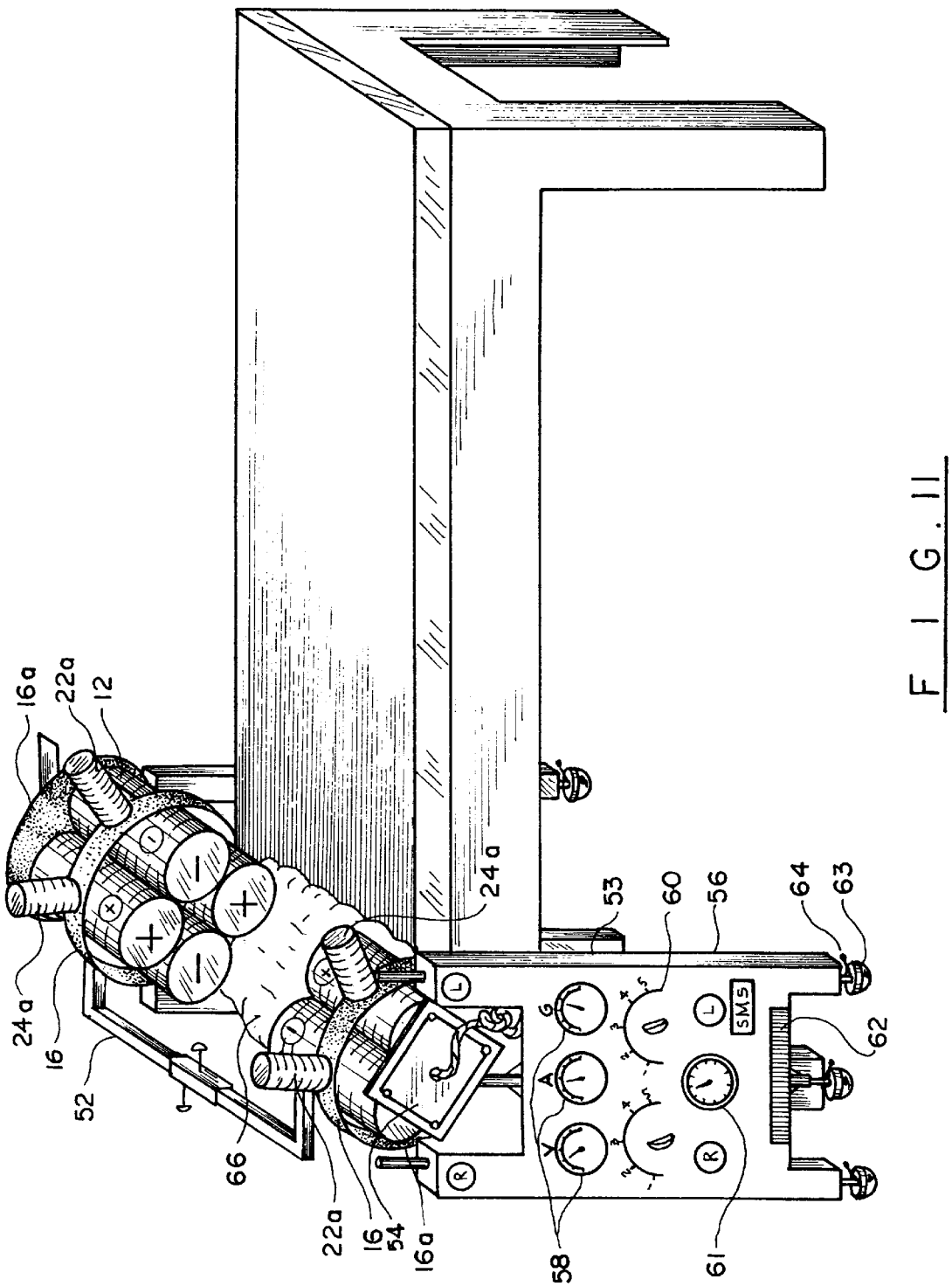

ELECTROMAGNETIC THERAPEUTIC TREATMENT DEVICE AND METHODS OF USING SAME

SPECIFICATION

This application incorporates by reference, and claims the benefit of, U.S. Provisional Patent Application Ser. No. 60/000,317, entitled "Treatment Device for Seizures and Cerebral Edema", filed Jun. 19, 1995; U.S. Provisional Patent Application Ser. No. 60/000,300, entitled "Treatment Device for Cardiac Dysrhythmia", filed Jun. 19, 1995; U.S. Provisional Patent Application Ser. No. 60/000,299; entitled "Treatment Device for Acute Burns", filed Jun. 19, 1995; U.S. Provisional Patent Application Ser. No. 60/000,318, entitled "Method of Improving Efficacy and Sensory Tolerance With a Continuous Pulse, Non-Modulating Non-Burst Mode Nerve Stimulator", filed Jun. 19, 1995; and U.S. Provisional Patent Application Ser. No. 60/001,012, entitled "Method of Inducing Regional Analgesia and/or Anesthesia With a Quadrapolar Static Magnetic Field Augmented by a Continuous Pulse, Non-Modulated Non-Burst Mode Nerve Stimulator", filed Jul. 10, 1995.

BACKGROUND OF THE INVENTION

1. Field of the Invention

The present invention relates to magnetic devices for therapeutic application to the human body, and more particularly to an electromagnetic quadripolar treatment device with a focusing means to increase the intensity, focus and gradient of the field for placement against or in proximity to the human body. The present invention further relates to methods of use of such magnetic treatment devices for the treatment of various animal diseases, complications and disorders such as such as, but not limited to, a) pain and swelling, b) cardiac dysfunction, c) drug resistant seizures and cerebral edema, d) pain and edema sustained in severe burns, e) potentiation of pharmaceutical agents, f) treatment of strokes and protection from cell death following hypoxic injury, g) control of edema and pain and speeding healing following surgical procedures and speeding healing rates of chronic non-healing wounds, and h) control of pain and sludging of sickled cells in sickle cell disease.

2. General Background

Magnetic fields have been applied to the human body for various therapeutic purposes for many centuries. For example, magnetic medical treatment devices for application against selected portions of the human body are disclosed in U.S. Pat. No. 3,921,620; method and apparatus for suppressing neuron action potential firings U.S. Pat. No. 5,312,321; magnetic plasters for improving circulation are disclosed in U.S. Pat. No. 4,489,711; magnetic fields for stimulation of bone growth are disclosed in U.S. Pat. No. 4,105,017; and magnetic stimulation of nerve cells has been accomplished with devices such as the Cadwell Magneto-Electric Stimulator (MES-10) manufactured by Cadwell Laboratories, Inc. of Kennewick, Wash.

Various disease states, tissue and organ malfunction may be the result of loss of membrane stability and normal permeability. These membranes may be cellular or intracellular, but in any case represent malfunction of excitable tissue. This malfunction of excitable tissue may be due to alteration of ion channel function. These various disease and states of malfunction may also be related to alteration of receptor sites or agonist sites of enzymes and/or other such dynamic systems within living organisms and more particularly the human animal. A great variety of symptoms and malfunctions may occur, such as, but not limited to, the above listed disease and/or disorder states.

Unfortunately, many types of ailments, including chronic pain, poor localized blood flow, cerebral edema and certain seizures and injuries cannot be successfully treated with conventional drug, physical therapy or surgical therapies. Because such ailments are often untreatable with conventional therapies, there is a need for alternative therapies that relieve these previously untreatable or poorly treatable conditions.

Accordingly, it is an object of this invention to provide a device that alters the stability of excitable membranes and other charged structures and systems in order to treat aliments of animals.

Another object of the invention is to provide an electromagnetic device for production of an electromagnetic field for treatment of such disorders, such a devise being electromagnetically powered, and having, inter alia, an alternating polarity, quadripolar array which generates a 3 dimensional, steep field gradient.

It is a further object of this invention to provide a device which contains a flux return ring on the back surface away from the body surface which is designed to return the magnetic flux thereby increasing the strength and gradient without altering the center charge and symmetry of the 3 dimensional steep gradient field.

Another object of the invention is to provide a flux focusing ring surrounding the DC electromagnetic coils on the outer perimeter stationed midway between the top and bottom of the flux core of the pole. Attachment means is provided to hold the focusing ring to the outer perimeter of the coils.

It is a further object of the invention to provide an electromagnetic pole of like polarity on the outer surface of each of the 4 poles of the invention such that the top of the core is oriented to the geometric side of the pole such that the axis of the two magnets form a 90° angle. The focusing magnet comprises an iron pole, an iron housing and a copper wire coil.

It is a further object of the invention to control each focusing magnet by a separate rheostat such that the focusing ring containing magnets can focus and balance the symmetry of the therapeutic field.

Additional object of the current invention is to present an array of embodiments for a variety of therapeutic purposes.

A further object of this invention is to reveal a method of design and manufacture of an iron core which will produce a center charging homogenous, static magnetic flux and decreased heat production from EMF induced adherent heat producing currents (referred to as Eddy Currents in AC EMF circuits). In AC circuits, "Eddy" currents are currents due to induced EMF and account for some of the losses in electrical equipment. If we consider a solid iron rotor of a generator or motor, the solid iron rotor cuts magnetic lines of force as it rotates the same as the wire coil of the rotor. The coil has an EMF induced in it in the direction as dictated by "Fleming's Rule" as the "left-hand rule." The iron core also has an EMF induced in it in the same direction as the coil. This iron core is a low resistance circuit and the current does no work, but merely heats the iron core. The current flow in the core generates a secondary magnetic flux which is of higher frequency than the 60 cycle current and is more aberrant due to the variable resistance of the non-homogenous iron. The higher frequency magnetic flux is erratic due to the reverberating nature of the "Eddy" Currents in the iron core. The resistance of any given position of the conductor in ohms divided into the electromotive force in volts is equal to the current flow in amperes. In the non-homogenous core with lack of continuity of the base-metal crystal structure. The heating effect of the current is proportional to the square of the current. These currents are commonly called "Eddy" currents, but are also known as Foucault currents.

The dominant thinking today suggests that such negative currents do not exist in DC electromagnetic circuits. In the current invention similar currents are a factor which must be dealt with in the design. The predecessor device of the current invention consists of a magnetic flux generator and a D/C static drive power source. The magnetic flux generator comprises a plurality of electromagnetic bodies having at least four magnetic poles substantially in a single plane, the magnetic poles being oriented to define the four vertices of a quadrilateral shape. The four magnetic poles comprise two positive and two negative poles, the two positive poles defining opposite diagonal vertices and the two negative poles defining opposite diagonal vertices of the quadrilateral shape. Each of the magnetic poles are magnetically attracted to the two oppositely charged poles and magnetically repelled by the like charged poles. Each of the electromagnetic poles include a conducting wire wound around a cast iron core. The wire may be comprised of any conducting material (copper or aluminum). The core and winding are supported by a cast iron housing. The poles are electrically wired in parallel and are charged by a DC power source. The cast iron housings and cores being porous, non-homogenous cast iron has varying resistivity and is the victim of mutual induction in adjoining coils. The induced current follows Flemming's rule. The induced current flows in opposite directions in the adjoining coils. In this system, the current flow in adjoining poles is in the opposite direction, therefore the induced current augments the current in adjoining poles and decrease the current in diagonally opposing poles. This lack of homogeneity in the iron conductor with fluxing resistivity (as a current flow pathway heats, the current flow finds a path of less resistance, the former path then tends to cool because of decreased current flow—the summation effect is seen as reverberation of resistance and therefore current flow [amps=Resistance in volts/ohms]) and unbalanced induction causes reverberation in the DC flux fields which moves lines of flux across the poles. This brings about an erratic EMF in the core and cast iron housing. We will call these higher frequency erratic currents "Holcomb's Currents." Work in human and animal models reveal that these currents cause heat generation in the poles and reduce or cancel beneficial therapeutic effects of the steep gradient three dimensional magnetic flux fields. These high frequency erratic currents can be minimized by a process of lamination. The lamination reduces magnetic hysteresis and erratic currents. Lamination can't be used, however, in this invention because it distorts the symmetry of the field.

Another object of the invention is to reveal a new process for the production of magnetically soft materials in which the continuity of the base-metal crystal structure is undisturbed and homogenous. A method of producing a course grain homogenous core is revealed. Suitable grain size is attained by grinding silicon electrical steel or Permalloy (a high nickel iron alloy) to a powder of suitable grain size, treated with a powerful, silica colloid polymer, placed into molds and annealed under high pressure. The resulting core is homogenous with uniform orientation of the base-metal crystal structure which provides crystal structure continuity, uniformity, low aberrant current formation and low hysteresis as well as high saturation of magnetic induction.

Various embodiments of the use of the electromagnetic field produced in the instant invention include the following, but are not limited to the following.

A. Pain and Swelling (SMS-P).

1. Acute Pain and Edema

It is a further object of the invention to provide a device that alters nerve cell behavior in a manner that reduces painful sensations.

Another object of the invention is to provide an apparatus for applying a variable symmetric quadripolar, three dimensional magnetic flux which is focused and balanced to the human body to stabilize excitable membranes and thereby reduce pain and edema associated with acute injury, inflammation or surgical procedure.

Another object of the invention is to provide a specialized magnetic flux field to control and reverse the swelling associated with acute injury, inflammation and surgery.

A further object of the invention is to provide a method for applying a therapeutic electromagnetic device to the human body to relieve pain, improve blood flow and reduce swelling associated with injury, surgery or acute inflammation.

2. Chronic Pain

It is a further object of the invention to provide a device that alters nerve cell behavior in cases of chronic pain to block the spontaneous pacemaker firing of the chronically malfunctioning pain fiber (mostly Aδ and C-fibers).

B. Magnetic Treatment Device for Cardiac Dysfunction Static Magnetic Stabilizer—(SMS-C).

This application of the present invention relates to magnetic devices for therapeutic application to the human body, and more particularly to an electromagnetic quadripolar treatment device for placement in an intensive care unit bed for the treatment and control of cardiac arrhythmia, improvement of cardiac blood flow and to control chest pain by applying the electromagnetic quadripolar flux generator either over or underneath the chest of a patient with acute myocardial infarction and/or arrhythmia. The three dimensional flux field gradient when applied to the area of the heart controls arrhythmia, improves blood flow, controls angina and protects ischemic myocardial muscle from cell death.

Myocardial infarction with secondary fibrillation and/or heart failure accounts for the leading cause of death in the United States. Myocardial infarction occurs secondary to occlusion of arterial blood supply to a portion of the myocardium. This occlusion can occur either secondary to blockage by atherosclerotic plaques and/or arterial spasm. This event results in chest pain, potential dysarrhythmia, potential fibrillation, and potential heart failure secondary to decrease in inotropic contraction of the myocardium. Each of these events are treated by drug intervention with varying success. In the event that the myocardium fibrillates, this constitutes a medical emergency of the greatest magnitude. The heart must be immediately defibrillated. The current therapy is to place a DC capacitor driven high voltage discharge across the myocardium by applying two paddles to the chest wall and discharging a surge of high intensity DC current. This surge of high voltage DC current will depolarize the myocardium and allow the fastest pacemaker tissue within the heart to assume pacemaker function i.e. the atrial pacemaker. In most instances the myocardium is so irritable and prone to recurrent spontaneous fibrillation that drugs such as I.V. xylocaine must be given to stabilize the electrically irritable myocardium. These drugs are mostly sodium channel blockers and as such they decrease the inotropic and chronotropic contraction of the myocardium. If inadvertent overdosage occurs, the pumping action of the heart may be decreased to below a critical level. Drugs such as epinephrine may need to be used to maintain blood pressure and increase the inotropic and chronotropic contraction of the heart, as well as to increase blood vessel tone. Revival of a patient who fibrillates as a consequence of a myocardial infarction requires rapid manipulation of D/C defibrillation and careful drug manipulation.

The current acute therapy for myocardial infarction and its frequent complications has many side effects. DC defibrillation of the heart causes myocardial damage with each exposure to the D/C discharge. Therefore with each needed defibrillation the chances of recovery progressively decrease. Use of xylocaine to stabilize the myocardium is accompanied by decrease in contraction of the myocardium and decrease in vascular tone. The subsequent use of epinephrine may induce fibrillation and increase the after load on the heart enough to cause congestive heart failure. This condition is clearly a life threatening disorder frequently resulting in death or permanent disability. Because this ailment is often poorly responsive to conventional therapy, there is a need for alternative therapy that will defibrillate the myocardium without cellular damage, stabilize the myocardium without decreasing the desired function, dilate the arteries of the heart for better blood flow, control myocardial pain and prevent cell death.

Accordingly, it is an object of this invention to provide a device that alters myocardial behavior in a manner which stops fibrillation, stabilizes the electrical activity, dilates myocardial arteries and controls chest pain which is secondary to ischemia. It is a further object of this invention to limit the extension of the infarction and to limit cell death which is secondary to ischemia.

Another object of the invention is to provide a magnetic device that alters myocardial behavior in a manner which controls myocardial ischemia, fibrillation, chest pain and extension of the infarction.

Another object of the invention is to provide a magnetic device that alters myocardial behavior by altering sodium and calcium channel functions such that the quadripolar, alternating polarity and the subsequent field gradient blocks varying degrees of sodium and calcium channel function. The degree of blockage is related to the gradient and strength of the field. The gradient and the field strength may be manipulated by this technology.

It is a further object of the invention to provide an apparatus for applying a variable magnetic flux to the human body in the area of the heart.

It is a further object of the invention to provide an apparatus for applying an instantaneous high intensity magnetic flux designed to defibrillate the myocardium of a human.

C. Magnetic Treatment Device for the Control of Drug Resistant Seizures and Cerebral Edema—Static Magnetic Stabilizer (SMS-E).

This application of the present invention relates to magnetic devices for therapeutic application to the human body, and more particularly to an electromagnetic dual quadripolar treatment device for placement on either side of the human head for control of seizure discharges and cerebral edema.

Seizure activity in the brain is a rather common occurrence. Clinical seizures result from uncontrolled firing of brain neurons. This uncontrolled spontaneous discharge may have projections to many parts of the brain, causing a variety of clinical presentations. These seizures are controlled in many patients by anticonvulsant drugs which work through the alteration of ion channels. The drugs increase the seizure threshold by stabilizing neuron cell wall permeability to ion flux. Many of these seizures are not well controlled by medication nor any other available modalities. A significant number of these seizures are resistant of all modalities of treatment. These patients present to the hospital in a state of continuous uncontrolled seizure activity. This condition is referred to as Status Epilepticus, which is a medical emergency requiring prompt attention. Patients in Status Epilepticus, if not controlled quickly, develop brain hypoxia and resultant hypoxic ischemic encephalopathy. This is a life threatening disorder, frequently resulting in severe brain damage or death. Because this ailment is often untreatable (drug resistant Status Epilepticus) by conventional drugs, there is a need for alternative therapies that stabilize the abnormal irritable neuron cell wall electrophysiology.

Accordingly, it is an object of the invention to provide a device that alters brain neuronal behavior in a manner which stops the abnormal electrical discharge of the neurons, therefore stopping the seizures Another object of the invention is to provide a magnetic device that alters brain neuronal behavior in a manner which stops and controls drug resistant seizures.

Another object of the invention is to provide a method for applying a "dual head" therapeutic electromagnetic device to the human head to relieve seizures.

It is a further object of the invention to provide an apparatus with two magnetic flux head generators made with opposite poles facing, having 4 poles per head and alternating polarity such that the field gradient will be enhanced and the total energy applied to the brain will be increased over that which may be delivered by a single head on the device.

D. Magnetic Treatment Device for Control of Pain and Edema Sustained in Severe Burns—Static Magnetic Stabilizer for Burns (SMS-B).

The present invention relates to magnetic devices for therapeutic application to the human body, and more particularly to an electromagnetic multiple quadripolar treatment device for placement on the human body for control of pain and edema sustained in sever burns.

Severe burns of the human body constitute a medical emergency. Shock secondary to pain is a problem of major magnitude. Shock from hypovolemia is very difficult to control. The burned skin, especially 2nd and 3rd degree burns, leak fluid, electrolytes and protein. These severe consequences of a severe burn are related to stimulation of pain fibers and loss of cell integrity. Current therapy consists of narcotic analgesics, replacement of water, electrolytes and protein, as well as body temperature regulation. These are supportive measures. There is a need for adjunctive therapies that control pain, repair membrane integrity, control edema and stimulate healing.

Accordingly, it is an object of the invention to provide a device that alters pain fiber firing, repairs membrane integrity, controls edema in the area of the burn and promotes healing.

Another object of the invention is to provide a magnetic device that alters the permeability of burn damaged cells such that they are less permeable to water, ions and protein.

Another object of the invention is to provide a method of applying a therapeutic electromagnetic device to the human body after a serious burn injury.

It is a further object of the invention to provide an apparatus with three movable magnetic flux head generators (with flux and power focusing means, to control the gradient and the power) made with the ability to rotate on each side of the burn bed up to 30° to 45° above the surface of the bed which contains a burn patient.

An additional object of the invention is to provide an apparatus with four magnetic flux head generators mounted on a rotating bar, having four poles per head and alternating polarity such that the field gradient will be enhanced and the total energy applied to the burned body will be increased in relationship to the degree of burn.

E. Magnetic Treatment Device for Potentiation of Pharmaceutical Agents (SMS-D).

The present invention relates to magnetic devices for therapeutic application to the human body, and more particularly to an electromagnetic quadripolar treatment device for placement on the human body for control of various disease processes through its interaction with drugs and drug receptors.

Pharmacological agents are used extensively in our society for a variety of diseases, injuries and infectious states. All drugs exert multiple effects on the living organism. The dominant and desired effect is referred to as the therapeutic effect, and the less dominant and undesirable effects are referred to as side effects. All drugs have side effects, many of which are dangerous and/or lethal. Drug effects are mediated by receptor interaction with a receptor agonist. This is an intermediate step in all drug effects.

Accordingly, it is an object of the invention to provide a device that alters receptor configuration and/or drug receptor interaction. The effects may be agonist or antagonist effects. That is, the interaction may potentiate or inhibit drug effects and/or side effects.

An additional object of the invention is to provide a magnetic flux device comprised of an apparatus with four focused magnetic head generators mounted on a flux return ring. These are then surrounded by a flux return focusing ring with a focusing head at a 90° angle to each pole. This device may be focused to any portion of the body, such as the head, in order to bring about potentiation of therapeutic effects of certain drugs.

It is a further object of the invention to present data which demonstrates the potentiation of phenytoin on the control of drug resistant seizures, the potentiation of lidocaine on inhibition of C-fiber firing and the blockage of activation of calcium channels in C-fibers by capsaicin.

F. Magnetic Treatment Device for Treatment of Strokes-For Protection from Cell Death Following Hypoxic Injury (SMS-S).

This application of the present invention relates to magnetic devices for therapeutic application to the human body, and more particularly to an electromagnetic dual quadripolar treatment device for placement on either side of the human head for the application of a quadrilateral, steep, three dimensional magnetic flux field gradient.

Cerebral ischemia can be either focal or global, implying hypoperfusion of the entire brain. Ischemia is secondary to reduction of cerebral blood flow either locally or globally. Histologically selective neuronal necrosis may occur even after brief periods of global ischemia, and after focal ischemia there may be regions of pan necrosis in the territory of the affected artery. Progressing stroke is an observed deterioration after the initial insult that can occur for 48 to 96 hours. This phenomenon is likely related to a combination of evolving thrombosis and progressive cell death. Cell death occurs secondary to hypoxia, spillage of excitatory neurotransmitters, and spillage of calcium secondary to dying cells in the region.

It is the purpose of this invention to present data on mice which demonstrates protection from cell death in animals who have demonstrable ischemia secondary to prolonged status epilepticus. Data will also be presented which demonstrates protection from brain cell death following direct injection of toxic amino acids into the lateral ventricles.

A further purpose of this invention are planned clinical trials for protection from cell death and the reduction of edema in intracranial hemorrhage, strokes and spinal cord injuries.

G. Magnetic Treatment Device of this Invention for Control of Edema and Pain as well as to Speed Healing Rates Following Surgical Procedures. Speed Healing Rates of Chronic Non-healing Wounds (SMS-O).

Following surgical procedures, pain, edema, hyperalgesia, healing rate and scar formation are for the large part not treatable except with time and the natural healing process. Non-healing or slowly healing wounds are treated in a variety of ways including hyperbaric oxygen. Non-healing of wounds is mostly due to poor circulation.

Accordingly, it is an object of this invention to provide a device that produces a three dimensional, magnetic, steep gradient, flux field generator for the purpose of therapeutic application to the human body in the area of a post surgical wound or a chronic non-healing wound. The purpose is to control pain, edema, hyperalgesia, speed healing rates, decrease scar formation and speed the healing of chronic wounds by increasing blood flow to the wound.

H. Magnetic Treatment Device of this Invention for the Control of Pain and Sludging of Sickled Cells in Sickle Cell Disease.

Sickle cell anemia is due to an abnormal amino acid sequence in the beta globin chain of adult type (A) hemoglobin. The sickling process is often initiated by low oxygen tension and low PH. The sickled cells obstruct small vessels, and infarcts are frequent. Infarction accounts for the abdominal pain, bone pain, and gradual decrease in the size of the spleen. Current treatment is instituted primarily for the crisis. There is no known effective method for reducing the rate of chronic hemolysis or preventing crisis. The current treatment of choice is red cell transfusion. Other measures are good hydration, oxygen, analgesics and in some cases corticosteroids. A number of antisickling drugs are under evaluation, but none look very promising.

Accordingly, it is another object of this invention to reveal a method of using the variable, quadripolar, three dimensional field gradient of the invention to control the sickling of the blood cells, control pain and sludging associated with sickle cell crisis, and the prophylactic use of the invention in the prevention of sickle cell crisis.

The above-described embodiments are merely provided as illustrative examples of the instant invention and are not intended to limit the scope or spirit of the instant invention.

SUMMARY OF THE PRESENT INVENTION

In accordance with the principles of the present invention as embodied and as broadly described herein, a therapeutic electromagnetic treatment device adapted for placement of at least four magnetic flux generator poles is applied such that they may be applied to the animal or human body as described for the various applications revealed herein. The device comprises a plurality of electromagnetic bodies in each head of the applications, having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles. Each of the electromagnetic poles include a conducting wire wound around a special iron core. The wire may be comprised of any conducting material (such as copper or aluminum). The core and winding are supported by attachment means and containment means to place the core and winding on a ferroconductive flux return ring on the back surface away from the body surface. This ferroconductive flux return ring is designed to return the magnetic flux thereby increasing the strength and gradient without altering the centered charge and symmetry of the 3 dimensional steep gradient magnetic flux field. The four poles of the magnetic flux generator head are provided with a flux focusing ring which surrounds the DC electromagnetic coils on the outer perimeter, stationed midway between the top and bottom of the flux core of the poles and being about two and one half inches (6.35 cm) wide and one half inch (1.27 cm) thick. Attachment means is provided to hold the focusing ring to the outer perimeter of the coils. Attached to the outer surface of the focusing ring are electromagnetic poles of the same polarity as the pole to which it relates. These are attached in proximity to each of the 4 poles of the invention, the top of the core is oriented to the geometric side of the poles such that the axis of the two magnets form a 90° angle. The focusing magnet comprises an iron pole, iron housing and copper wire coil. A power means is provided to energize these focusing magnets with control means through a servo slave mechanism in order to adjust the power in relation to the gradient and energy in the primary core. Containment means are provided for holding the magnetic bodies in the desired configuration, and power means are provided for energizing the primary electromagnetic bodies. An array of containment means, support means, energizing means and control means of the embodiments will be presented for a variety of therapeutic purposes along with supporting data for the application.

A. Pain and Swelling

In accordance with the principles of the present invention as embodied and as broadly described herein, a therapeutic electromagnetic treatment device adapted for placement against the bodies of living animals is provided. The device comprises a plurality of electromagnetic bodies having at least two positive and two negative magnetic poles substantially in a single plane, the magnetic poles being oriented to define the four vertices of a quadrilateral shape, the two positive poles defining opposite diagonal vertices and the two negative poles defining opposite diagonal vertices of the quadrilateral shape. Each of the magnetic poles being magnetically attracted by the two oppositely charged poles and being magnetically repelled by the like charged pole. Containment means are provided, along with a flux return means, for holding the magnetic poles of the magnetic bodies in the desired configuration, and power means are provided for energizing the electromagnetic bodies, as well as energizing the flux focusing apparatus.

Preferably, the plurality of magnet bodies comprise four substantially identical electromagnets, two of which having a positive pole, two of which having a negative pole and all in a single plane. Each of the four electromagnets generate a magnetic flux field when energized. It is further preferred that the containment means be that which comprises a flux return ring and a focusing ring mounted on a support structure adapted to align the four electromagnets against the body of a living animal. The support structure may, for example, comprise a treatment table or a treatment chair to which the electromagnets are movably attached.

The accompanying drawings, which are incorporated in and constitute a part of this specification, illustrate presently preferred embodiments of the invention, and together with the description, serve to explain the principles of the invention.

B. Magnetic Treatment Device for Cardiac Dysfunction—Static Magnetic Stabilizer (SMS-C).

In accordance with the principles of the present invention as embodied and as broadly described herein, a therapeutic electromagnetic treatment device adapted for placement against the bodies of living animals is provided. The device comprises a plurality of electromagnetic bodies having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape. Each of the magnetic poles being magnetically attracted by the oppositely charged poles and being magnetically repelled by the like charged poles. Containment means are provided for holding the magnetic bodies in the desired configuration and power means are provided for energizing the electromagnetic bodies, as well as containment means and power means to energize and control the flux field, i.e. size, gradient and strength.

Preferably, the plurality of magnetic bodies in the flux generator head comprise four substantially identical electromagnets, two of which having a positive pole and two of which having a negative pole all in a single plane, each of the four electromagnets generate a magnetic flux field when energized. It is further preferred that the containment means be mounted on a support structure adapted to align the four electromagnets in a parallel plane with the surface of the containment bed or treatment structure.

The accompanying drawings, which are incorporated in and constitute a part of this specification, illustrate presently preferred embodiments of the invention, and together with the description, serve to explain the principles of the invention.

C. Magnetic Treatment Device for the Control of Drug Resistant Seizures and Cerebral Edema—Static Magnetic Stabilizer (SMS-E).

In accordance with the principles of the present invention, as embodied and as broadly described herein, a therapeutic electromagnetic treatment device adapted for placement of each of two magnetic heads on either side of the head of living animals is provided. The device comprises a plurality of electromagnetic bodies in each head, having at least two positive and two negative magnetic poles substantially in a single plane, these magnetic poles being oriented to define the four vertices of a quadrilateral shape, the two positive poles define opposite diagonal vertices, and the two negative poles define opposite diagonal vertices of the quadrilateral shape, each of the magnetic poles being magnetically attracted by the oppositely charged poles and being magnetically repelled by the like charged poles. Containment means are provided for holding the magnetic bodies in the desired configuration and power means are provided for energizing the electromagnetic bodies. Support means and power means are provided for the flux management system, i.e. flux return ring, flux focusing ring and flux focusing magnets.

Preferably, the plurality of magnet bodies in each head comprise four substantially identical electromagnets, two of which having a positive pole and two of which having a negative pole all in a single plane, each of the four electromagnets generate a magnetic flux field when energized. It is preferred that the containment means be mounted on a support structure adapted to align the four electromagnets in a parallel plane facing the 2nd quadripolar magnetic head such that opposite poles are facing i.e. attracting. The support structure may comprise a metal stand on rollers which would contain a means to attach it to the stand of the 2nd quadripolar cluster (underneath the bed or above the bed of a patient).

The accompanying drawings, which are incorporated in and constitute a part of this specification, illustrate presently preferred embodiments of the invention, and together with the description, serve to explain the principles of the invention.

D. Magnetic Treatment Device for Control of Pain and Edema, Sustained in Severe Burns—Static Magnetic Stabilizer for Burns (SMS-B).

In accordance with the principles of the present invention, as embodied and as broadly described herein, a therapeutic electromagnetic treatment device adapted for placement of at least four magnetic flux generator heads applied such that they rotate in an arc of 200° around a living animal as provided. The device comprises a plurality of electromagnetic bodies in each head, having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles. Containment means are provided for holding the magnetic bodies in the desired configuration, and power means are provided for energizing the electromagnetic bodies. Support means and power means are provided for the flux return ring, flux focusing ring and flux focusing magnets.

Preferably, the plurality of magnetic bodies in each head comprise four substantially identical electromagnets, two of which having a positive pole and two of which having a negative pole all in a single plane, each of the 4 electromagnets generating a magnetic flux field when energized. It is further preferred that the containment means be mounted on a support structure adapted to align the four electromagnets flux generator heads such that they may be rotated on a single support bar. The support structure may comprise a metal bar which would contain a means to attach it to the head and foot of the bed (underneath the bed of a patient).

The accompanying drawings, which are incorporated in and constitute a part of this specification, illustrate presently preferred embodiments of the invention, and together with the description, serve to explain the principles of the invention.

E. Magnetic Treatment Device for Potentiation of Pharmaceutical Agents (SMS-D).

In accordance with the principles of the present invention as embodied and as broadly described herein, a therapeutic electromagnetic treatment device adapted for placement against the bodies of living animals is provided. The device comprises a plurality of electromagnetic bodies having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles.

Preferably, the plurality of magnet bodies in each head comprises four substantially identical electromagnets, two of the electromagnets having a positive pole and two of the electromagnets having a negative pole all in a single plane, each of the four electromagnets generating a magnetic flux field when energized. It is further preferred that the containment means be in part a flux return ring and a flux focusing ring mounted on a support structure adapted to align the electromagnets such that specific portions of the human body may be treated with the quadripolar, three dimensional magnetic flux field gradient. The said magnetic flux field generation alters receptor configuration and/or drug receptor interaction. The effects may be agonist or antagonist effects, therefore the magnetic field pharmacologic interaction may potentiate or inhibit drug effects and/or side effects.

F. Magnetic Treatment Device for Treatment of Strokes—For Protection from Cell Death Following Hypoxic Injury (SMS-S).

In accordance with the principles of the present invention, as embodied and as broadly described herein, a therapeutic electromagnetic treatment device adapted for placement of each of two magnetic heads on either side of the head of living animals is provided. The device comprises a plurality of electromagnetic bodies in each head, having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles. Containment means are provided for holding the magnetic bodies in the desired configuration, and power means are provided for energizing the electromagnetic bodies, as well as containment and power means for the flux return ring, the flux focusing ring and the flux focusing magnets.

Preferably, the plurality of magnet bodies in each head comprise four substantially identical electromagnets, two of the electromagnets having a positive pole and two of the electromagnets having a negative pole all in a single plane, each of the four electromagnets generating a magnetic flux field when energized. It is further preferred that the containment means be mounted on a support structure adapted to align the four electromagnets in a parallel plane facing the 2nd quadripolar magnetic head such that opposite poles are facing i.e. attracting. The support structure may comprise a metal stand on rollers which would contain a means to attach it to the stand of the 2nd quadripolar cluster (underneath the bed or above the bed of a patient).

The magnetic flux field of the invention as described herein is applied to the human head and/or spinal cord to protect from cell death with evolving strokes or hypoxic ischemic brain insult with associated deficit.

The accompanying drawings, which are incorporated in and constitute a part of this specification, illustrate presently preferred embodiments of the invention, and together with the description, serve to explain the principles of the invention.

G. Magnetic Treatment Device of the Invention for Control of Edema and Pain as well as to Speed-Healing Rates Following Surgical Procedures and to Increase Healing Rates of Chronic Non-Healing Wounds (SMS-O).

In accordance with the principles of the present invention as embodied and as broadly described herein, a therapeutic electromagnetic treatment device adapted for placement against the bodies of living animals is provided. The device comprises a plurality of electromagnetic bodies having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles.

Preferably, the plurality of magnet bodies in each head comprises four substantially identical electromagnets, two of the electromagnets having a positive pole and two of the electromagnets having a negative pole all in a single plane, each of the four electromagnets generating a magnetic flux field when energized. It is further preferred that the containment means be in part a flux return ring and a flux focusing ring and flux focusing magnets mounted on a support structure adapted to align the electromagnets such that specific portions of the human body may be treated with the quadripolar, three dimensional magnetic flux field gradient. The said magnetic flux field, when applied to the area of insult on the animal or human body, will control edema and pain, and speed healing following surgical procedures. It will also increase healing of chronic non-healing wounds.

H. Magnetic Treatment Device of this Invention for the Control of Pain and Sludging of Sickled Cells in Sickle Cell Disease (SMS-SC).

In accordance with the principles of the present invention as embodied and as broadly described herein, a therapeutic electromagnetic treatment device adapted for placement against the bodies of living animals is provided. The device comprises a plurality of electromagnetic bodies having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged pole.

Preferably, the plurality of magnet bodies in each head comprises four substantially identical electromagnets, two of the electromagnets having a positive pole and two of the electromagnets having a negative pole all in a single plane, each of the four electromagnets generating a magnetic flux field when energized. It is further preferred that the containment means be in part a flux return ring and a flux focusing ring as well as 4 focusing magnets mounted on a support structure adapted to align the electromagnets such that specific portions of the human body may be treated with one or more of the quadripolar, 3 dimensional magnetic flux field gradient heads. The preferred embodiment contains 3 or more flux field gradient heads in a support means such as a table or bed. The position of the heads are controlled by a bedside controller such that they may be located to the area of pain in a patient in sickle cell crisis. The device may also be used prophylactically on a twice daily basis to prevent sickling attacks.

BRIEF DESCRIPTION OF THE DRAWINGS

A. Pain and Swelling.

FIG. 6 is a perspective view of another preferred embodiment of the electromagnetic treatment device of the invention.

FIG. 11 is a perspective view of a preferred embodiment of the electromagnetic treatment device of the invention.

DETAILED DESCRIPTION OF THE PREFERRED EMBODIMENT

Figure 1:
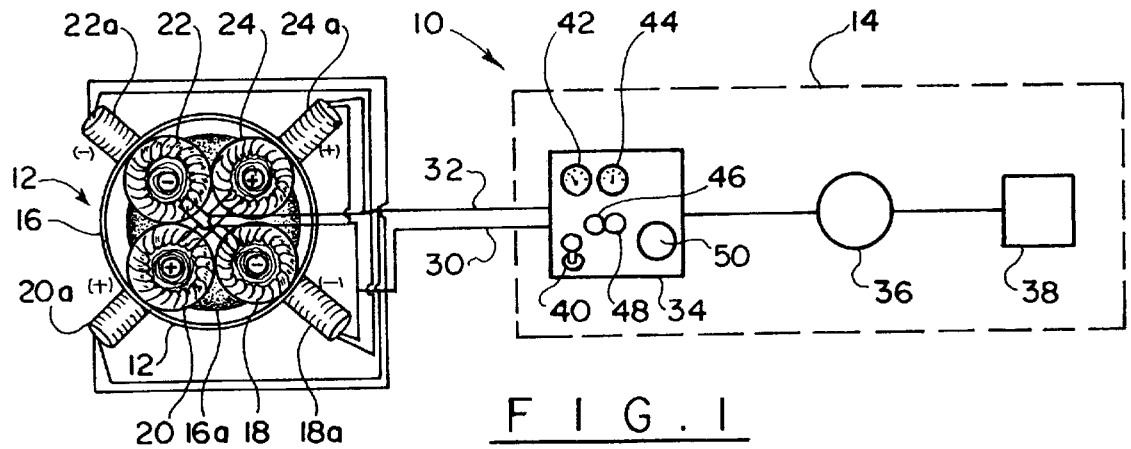
FIG. 1 is a schematic diagram of the various components of the electromagnetic treatment device of the invention, including the flux focusing components.

Reference will now be made in detail to the presently preferred embodiments of the invention, examples of which are illustrated in the accompanying drawings. Throughout the drawings like reference characters are used to designate like elements for each of the embodiments.

A. Pain and Swelling (SMS-P).

The electromagnetic treatment device of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite diagonal vertices of the quadrilateral shape. Each of the magnetic poles are magnetically attracted to the two oppositely charged poles and magnetically repelled by the like charged poles. Containment means hold the magnetic poles of the magnetic bodies in the above described configuration. Attached to the containment means are three (3) important and function altering components of the technology. Flux return ring 16a is attached to the bottom of the described 4 electromagnetic heads, this ring enhances the flux field and controls unwanted stray induction currents as well as stray flux from the opposite pole. A flux focusing ring 16 is positioned around the flux heads adjacent to the insulated wire coils, it being about 2.5 inches wide (6.35 cm) and ¼ to ½ inches (6.35 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45° to 90° angle to the long axis of the primary flux pole. In this position, the flux focusing coils along with the focusing ring, the flux return ring and the new iron core of this invention make the gradient steeper, increase the field strength and decrease healing and stray high currents. The flux return ring and the flux focusing ring are grounded to reduce stray induction currents and the variables that they add to the therapeutic magnetic field.

Figure 2:
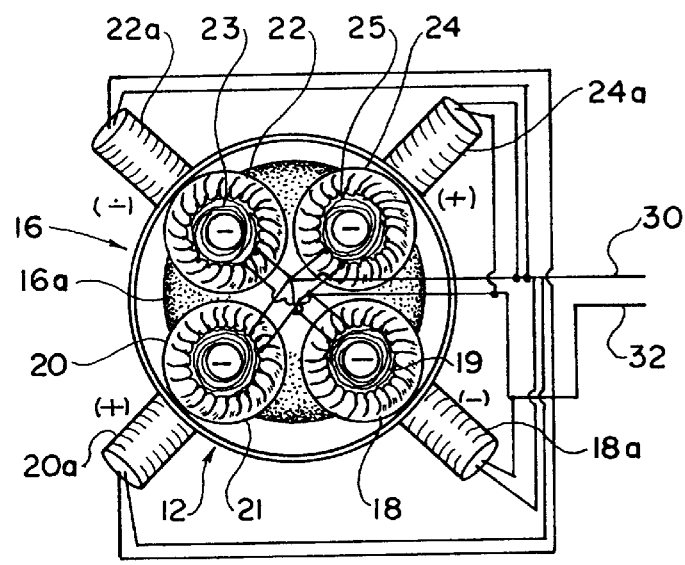
FIG. 2 is a plan view of the four electromagnets of one preferred embodiment of the electromagnetic treatment device of the invention along with the flux focusing components.
Figure 3:
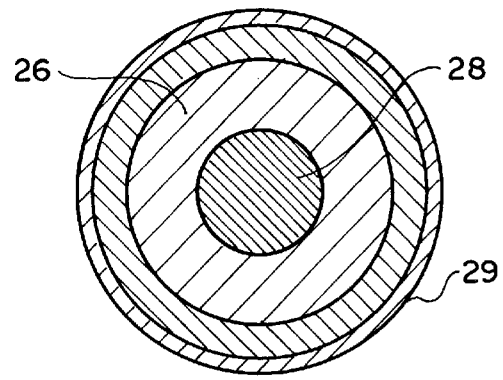
FIG. 3 is a perspective view of one of the electromagnets shown in FIG. 2 with the insulation cut away to better see the wire coil.

As embodied herein and schematically represented in FIGS. 1 and 2, magnetic flux generator 12 comprises four substantially identical electromagnetic bodies 18, 20, 22 and 24 held on a containment structure. The containment structure may comprise a mounting board, a casing or any other structure that will hold electromagnetic bodies 18, 20, 22 and 24 in the desired configuration. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 preferably comprise electromagnetic heads as best shown in FIGS. 2 and 3. Each electromagnetic head includes a conducting wire 26 wound around a cast iron core 28. Wire 26 may be comprised of any conducting material, as for example, copper or aluminum. For example, FIG. 3 shows a suitable electromagnet made using a five inch (12.7 cm) outer diameter and with a two inch (5.08 cm) center core 28 and a one and one half inch (3.81 cm) coil space with 3200 turns of #22 copper wire and covered with insulation 29. As shown in FIG. 2, coils 19, 21, 23 and 25 of electromagnetic heads 18, 20, 22 and 24, respectively, are each connected to a power source by wires 30 and 32.

The conducting wire 26 is wound around a porous cast iron core 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core be circular.

Figure 4:
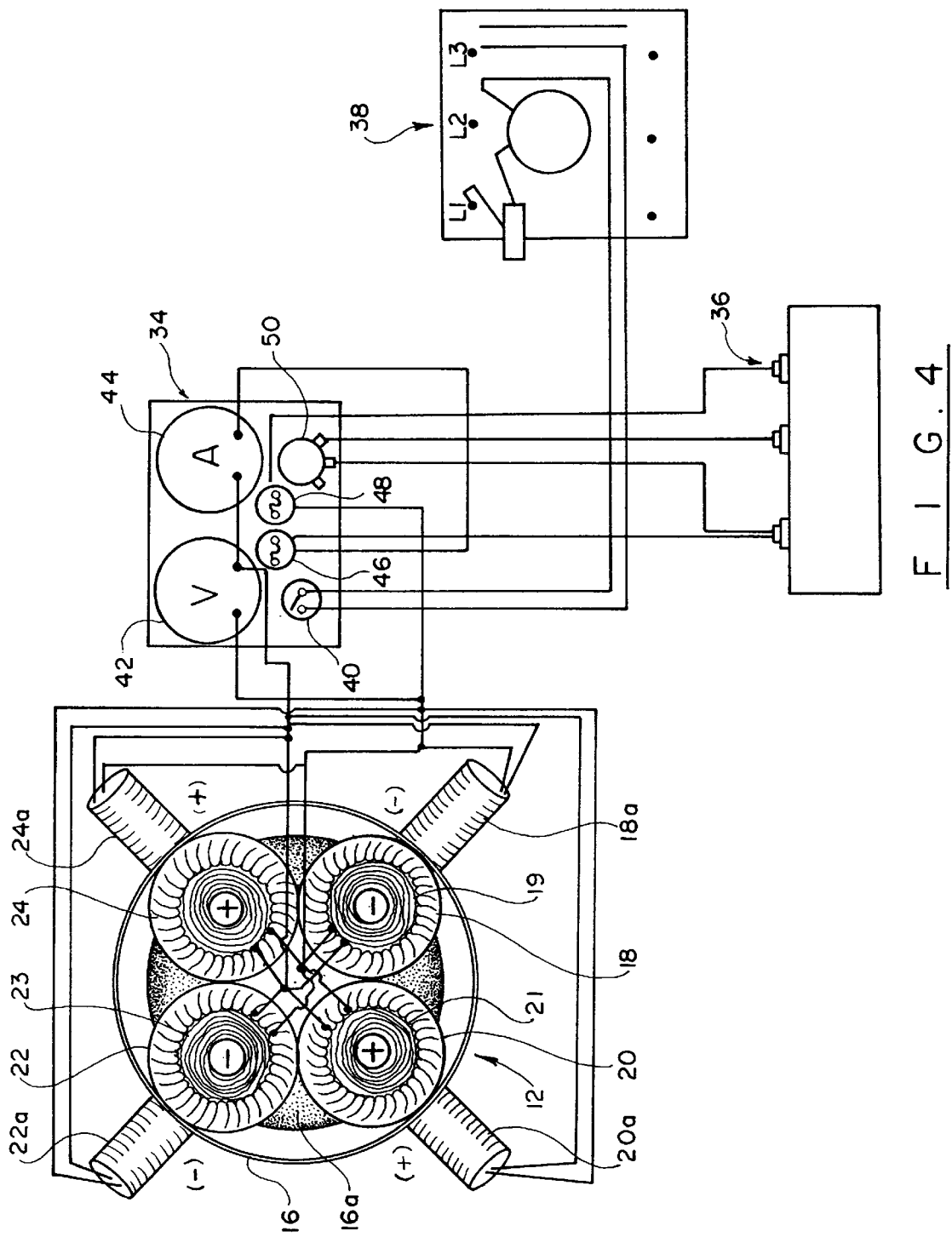
FIG. 4 is a schematic diagram showing electrical connections between the components of the electromagnetic treatment device of the invention.

According to the invention as represented in FIG. 4, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably powered by an alternating current motor, such as a 220 amp AC motor. It is preferred that generator 36 be capable of producing a 30 amp, 120 volt DC current. Control unit 34 includes an on-off power switch 40 for controlling the flow of direct electric current to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Rheostat 50 is preferably embodied as any conventional rheostat having a 50 amp, 120 volt capacity. As shown in FIGS. 1 and 2, each of the magnetic heads 18, 20, 22 and 24 may be electrically connected with power controller 34 by a single pair of wires 30 and 32. Preferably, each of the magnetic heads 18, 20, 22 and 24 may be individually regulated such that symmetric magnetic power may be balanced among all heads. It is anticipated that each magnetic treatment head could alternatively be individually connected to one of four rheostats in control unit 34 such that electric current supplied to each individual treatment head could be individually regulated.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each head generates a positive magnetic field, a negative magnetic field, or some combination thereof.

Figure 5:
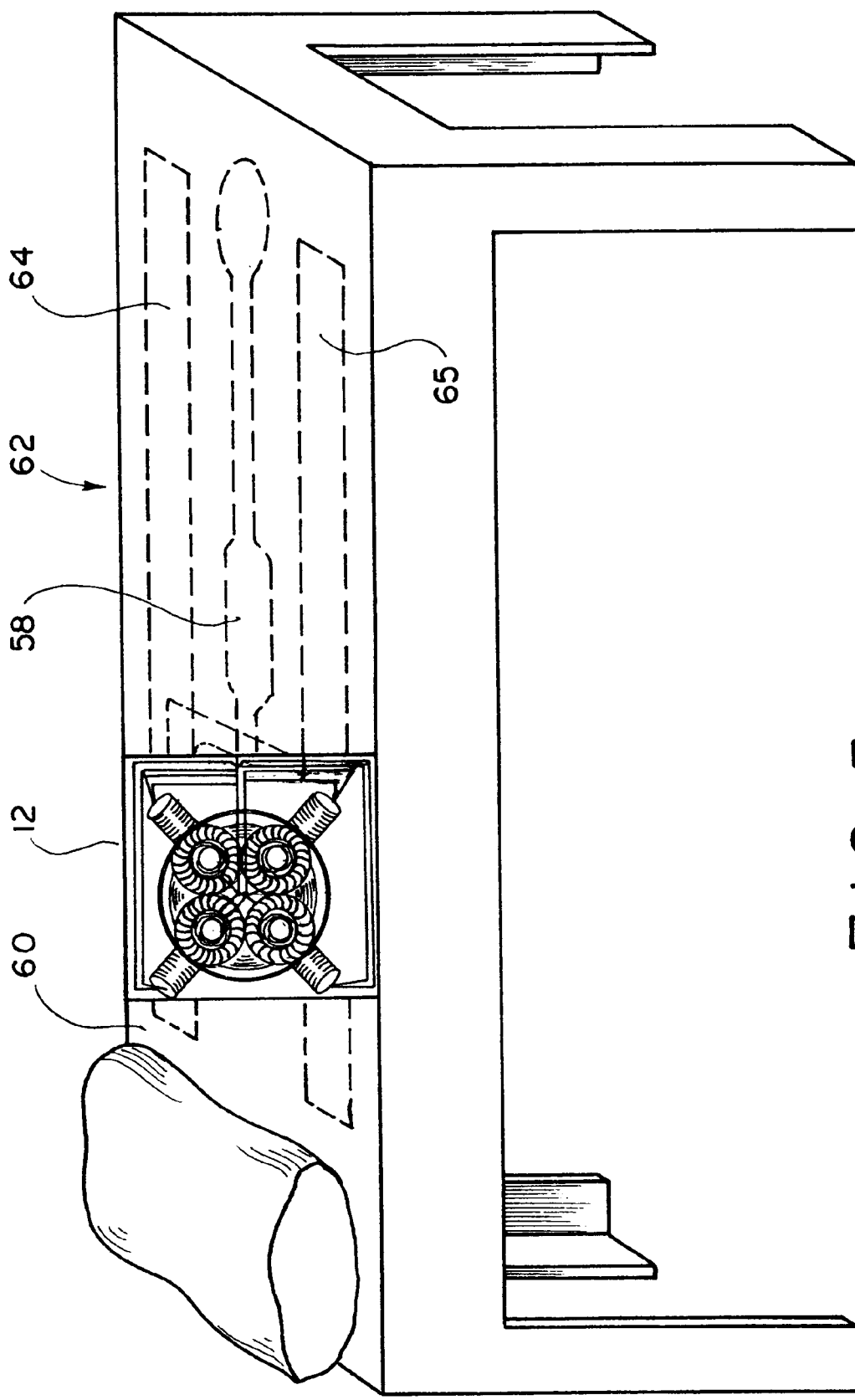
FIG. 5 is a perspective view of a preferred embodiment of the electromagnetic treatment device of the invention.
Figure 7:
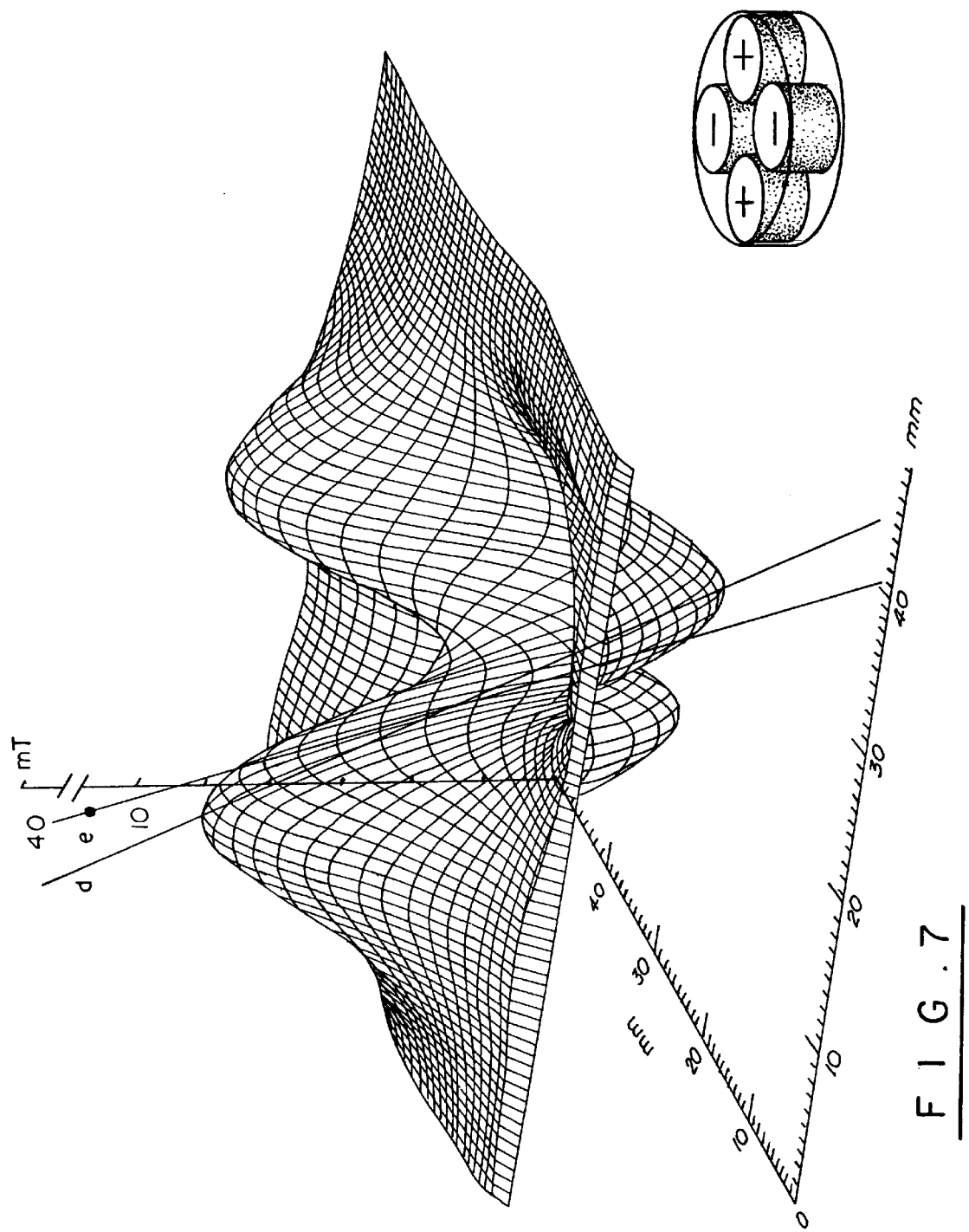
FIG. 7 is a diagram of the positive field of the invention, line e—e reveals a steeper slope of the field gradient over d—d by merely increasing the magnitude of the peak flux; it is a graphic depiction of data which reveals field intensity as determined by scanning in a systemic parallel plane 0.3 cm above the surface of the Magna Bloc™TMNS device with a "Hall Effect" probe and a standard gauss meter; it further demonstrates the increase in the slope of the gradient as the field intensity is increased; this field is identical to the electromagnetic field of the invention.

According to the invention, the therapeutic electromagnetic treatment device of the invention may be mounted on a support structure adapted to align the four electromagnets against the body of a living animal. As embodied herein, the support structure may comprise a bench, table, bed, chair or other similar assembly. FIG. 5 shows an elongated treatment table support structure 62 having a magnetic flux generator 12 affixed to the bottom surface thereof. Flux generator 12 is preferably powered by a power source (not shown) like that described above. Flux generator 12 moves laterally along the bottom surface of table 62 on rails 64 and 65. Flux generator 12 may be moved manually or by a power driven actuating mechanism 58 such that flux generator 12 may be aligned with a desired portion of a human or animal body to which magnetic flux is to be applied. A magnetic flux field is generated by each of the electromagnetic heads on flux generator 12 when the electromagnetic heads are energized. A magnetic flux field so generated by the electromagnetic heads extends above a top planar surface 60 of table 62 such that magnetic flux impinges upon a body on the table surface.

The therapeutic electromagnetic treatment device of the invention may be otherwise supported by a chair structure, as shown in FIG. 6. Chair 162 includes a seating surface 164 and a vertical back support surface (not shown) and a magnetic flux generator 12. Flux generator 12 moves vertically on rails 66 and 68 in a cavity in the back of chair 162. Flux generator 12 is powered by a power source (not shown) like that described above. The power source may be incorporated in the bottom of chair 162 or may comprise an independent unit. Flux generator 12 may be mounted for manual vertical movement within chair 162 or for automatic movement by a power driven actuating mechanism 70.

The electromagnetic treatment device of this invention has been beneficially applied to the human body to reduce pain, reduce fatigue and improve blood circulation. Several case histories are set forth below.

CASE 1

A 73 year old female presented with a fourteen year history of severe rheumatoid arthritis of the cervical, thoracic and lumbar spine with progressive pain, stiffness and decreasing mobility. She required assistance to ambulate.

Examination revealed diminished respirations secondary to thoracic radicular pain, decreased range of motion in neck, shoulders and extremities. Both knees were painfully swollen and inflamed.

Medical history revealed she had a total right knee replacement four years prior. She was presently being evaluated for a left total knee replacement. She was on a non-steroidal, anti-inflammatory medication with minimal control of symptoms.

Treatment with local quadripolar permanent magnetic devices as described in U.S. patent application Ser. No.

07/171,837 was instituted with excellent pain control reported. Swelling in both knees was reduced and the inflammation disappeared. She continued to take non-steroidal, anti-inflammatory medication concomitantly with the magnetic therapy. She had excellent control of symptoms for 2½ years when she experienced an exacerbation of symptoms in the thoracic area with radiculopathy.

Therapy was instituted in her home using the electromagnetic treatment device installed in a recliner chair as shown in FIG. 6. Within a few minutes after treatment had begun, the pain subsided. Within 24 hours of treatment, significant range of motion in the thoracic spine, shoulders and neck returned. Within one week of treatment she had full range of motion in the extremities with sustained improvement.

She had continued to be treated utilizing the electromagnetic device for four months, 3–4 times a day, 30–45 minutes per treatment. She reports she is pain free, ambulates well without assistance, and has no joint swelling or inflammation.

CASE 2

A 54 year old female presented with a 10 month history of acute disc herniation with spinal contusion, with surgical intervention, with resultant cord ischemia. She had secondary left thoracic radiculopathy and a sympathetically maintained pain syndrome.

Physical examination revealed scoliosis secondary to muscle spasms. She was receiving pain medication therapy with little relief. She ambulated only with assistance and was unable to carry on normal activities of daily living.

Treatment with the local permanent magnetic devices as described in U.S. patent application Ser. No. 07/171,837 was instituted. She reported from 40%–60% pain reduction for six months. She resumed some routine daily activities. She was evaluated for possible neuro-surgical intervention for remaining pain. A dorsal root entry zone procedure was performed to relieve the radicular and sympathetic pain over the nerve distribution at Thoracic 9, 10, 11 on the left.

The motor tracts were apparently inadvertently overheated during the surgical procedure resulting in plegia of the left lower quadrant including the left lower abdomen, hip, pelvis and leg. She had lost control of bowel and bladder function. After the edema post surgery subsided, she had minimal return of function of left lower quadrant and bowel and bladder function.

She was discharged from the hospital with little hope of recovery. Physical therapy was begun concomitant with treatment with the electromagnetic treatment device installed in a bed as shown in FIG. 5.

She has progressively improved with decrease in pain, increased motor strength and has regained total control of bowel and bladder function.

She has been treated from 1–4 hours a day for approximately five months. If treatment of the electromagnetic device is interrupted greater than 48 hours, she has an acute exacerbation of symptoms with increased pain, left sided decreased muscle strength and spasticity of abdominal muscles of hip flexors, dorsal flexors of the foot and less control of bodily functions.

CASE 3

A 55 year old female presented with a 2 year history of severe Causalgia at Thoracic 9, 10 and 11 with left radicular thoracic somatic and sympathetic pain.

MRI, CT and EMG were negative. She had received multipharmacological therapy with narcotics, non-narcotics pain medication, steroids, non-steroidal, anti-inflammatory drugs and others with little pain relief.

Treatment with the local quadripolar permanent magnetic devices as described in U.S. patent application Ser. No. 07/171,837 concomitantly with the electromagnetic treatment device installed in a table was instituted. The devices were worn on a continuous basis. She has received electromagnetic therapy on an average of 4 times a week for 30 minutes to 1 hour for four months.

She reports variable pain reduction post treatment with the electromagnetic device by 50%–90%. After she has been without electromagnetic therapy for 36–48 hours, her pain intensity worsens. She estimates an overall pain reduction at 40%.

CASE 4

A 67 year old male presented with a 20 year history of Osteoarthritis of the lumbar sacral spine and feet with progressive severe foot and low back pain. Work history revealed that his job required standing on concrete floors from 8–10 hours a day. Therapy was instituted in his home using the electromagnetic treatment device installed in a recliner chair as shown in FIG. 6. He was treated once a day at night for 30 minutes to 1 hour. Pain was relieved after the first treatment with sustained relief. He has undergone daily treatments for two months and has reported no exacerbation of pain.

CASE 5

A 48 year old white male with a history of severe atherosclerosis, coronary artery bypass grafts and stroke presented with painful, cold, blue feet and legs.

Physical examination revealed good pulse but poor small vessel circulation in the lower extremities. The patient was treated in the lower back on the posterior surface with the electromagnetic unit shown in FIG. 5 for 30 minutes. After about 3 minutes, the patient experienced improved color, warming and a sensation of warmth in the feet and legs. This sensation continued to improve with excellent return of color and warmth over the 30 minutes of treatment. These improvements lasted for approximately 4 hours and resulted in longer durations with additional treatments.

CASE 6

A 63 year old white male presented with a 5 year history of cold feet accompanied by burning paresthesias of the feet. He had been a heavy cigarette smoker. On examination, he had no neurological deficits and had a moderately good dorsalis and posterior pedal pulse. He had marked decrease in small vessel circulation. The patient's lumbosacral area was placed on the electromagnetic device shown in FIG. 5 for 30 minutes. The patient experienced complete reversal of the burning paresthesias and warming of the feet. This improvement was sustained for 3 to 4 hours and the effect was prolonged with repeated treatments.

The beneficial effects of the electromagnetic treatment device of the present invention, at least in part, are brought about by the quadripolar, alternating, center charged, symmetric, static magnetic field impinging upon the cell walls of cells. The steep gradient of these fields brings about a polarization of the lipoprotein matrix of the cell wall such that sodium and calcium channels are blocked in such a fashion as to impede the flux of these ions. Impedance of ion flux blocks the pacemaker effect of damaged or insulted neuronal cell wall membranes (i.e., blocks initiation of a spontaneous depolarization). The control of spontaneous depolarization of neurons brings about: (1) control of pain, and (2) dilatation of peripheral blood vessels by inhibiting excessive outflow of sympathetic nervous discharge to the vessels. This inhibition of sympathetic firing brings about dilatation of the blood vessels. The effect of calcium channel blockade brings about local dilatation blockade brings about local dilatation of vascular smooth muscles and therefore improved blood flow. A portion of the pain relief is likely to be a result of improved blood flow.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the four magnetic poles include two positive and two negative poles, the two positive poles defining opposite diagonal vertices and the two negative poles defining opposite diagonal vertices of the quadrilateral shape, each of the magnetic poles being magnetically attracted by the two oppositely charged poles and being magnetically repelled by the like charged pole.

Still further, the therapeutic electromagnetic treatment device described above wherein the plurality of electromagnetic bodies comprise four substantially identical electromagnets, two of the electromagnets having a positive magnetic pole in the substantial ly single plane and two of the electromagnets having a negative magnetic pole in the substantially single plane, each of the four electromagnets generating a magnetic flux field when energized by the power means.

Also embodied is the therapeutic electromagnetic treatment device described above wherein the four electromagnets each comprise a cast iron core wound with electrically, conducting wire.

Further, the electrically conducting wire of the therapeutic electromagnetic treatment device can be copper or aluminum wire.

Additionally, the quadrilateral shape of the therapeutic electromagnetic treatment device can be a parallelogram shape; further, the parallelogram shape can be a rectangle shape or a square shape.

Still further, the power means of the therapeutic electromagnetic treatment device can comprise a direct current generator and the power means can be electrically connected to each of the four electromagnets.

The therapeutic electromagnetic treatment device can also comprise a power control means for controlling the amount of electrical power supplied to each of the four electromagnets so as to regulate the magnetic flux field generated by each of said four electromagnets.

In a preferred embodiment, the therapeutic electromagnetic treatment device of can be mounted on a support structure adapted to align said four electromagnets against the body of a living animal.

The therapeutic electromagnetic treatment device support structure can also comprise an elongated planar table having a first planar surface, the first planar surface of the table being adapted for supporting the body of a living animal against which the four electromagnets are placed, the containment means being movably attached to the planar table for movable alignment with select portions of the living animal body, the magnetic flux field generated by each of the four electromagnets extending above the first planar surface of the table when the four electromagnets are energized by the power means.

Further, the planar table of the therapeutic electromagnetic treatment device can have a cavity in which the containment means is movably mounted. Also, the planar table of the therapeutic electromagnetic treatment device can have a second planar surface opposite the first surface, the containment means being movably mounted on the second planar surface.

The support structure of the therapeutic electromagnetic treatment device can comprise a chair having a substantially horizontal seating surface and a substantially vertical back support surface, the seating and back support surfaces adapted for supporting the body of a living animal against which the four electromagnets are placed, the containment means being movably attached to the chair for movable alignment with select portions of the living animal body, the magnetic flux field generated by each of the four electromagnets extending out from the substantially vertical back support surface when the electromagnets are energized by the power means.

The chair of the therapeutic electromagnetic treatment device can also have a vertically extending cavity behind the vertical back support surface and the containment means can be mounted for vertical movement within the cavity.

Further, the therapeutic electromagnetic treatment device can further comprise an electrically powered means for moving the containment means vertically and horizontally within the vertically extending cavity.

Still further, in a preferred embodiment, a method of therapeutically placing an electromagnetic treatment device against the human body to relieve pain, may comprise the steps of: assembling at least one group of electromagnetic bodies having at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices of the two negative poles defining opposite vertices of the rectangular shape; fixing the orientation of the plurality of magnetic bodies in a single containment body; selectively placing the containment body at a position against the human body over an area producing pain sensations; and energizing the magnetic bodies with electric power so that each of the magnetic bodies generate a magnetic flux field.

Further, a method of therapeutically placing an electromagnetic treatment device against the human body to improve blood circulation, can comprise the steps of: assembling at least one group of electromagnetic bodies having at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body at a position against the human body over and area producing pain sensations; and energizing the magnetic bodies with electric power so that each of the magnetic bodies generate a magnetic flux field.

It will be apparent to those skilled in the art that modifications and variations can be made in the electromagnetic treatment device and method for applying the electromagnetic treatment device of the present invention. The invention in it boarder aspects, therefore, is not limited to the specific details, representative methods and apparatus and illustrative examples shown and described above. Thus, it is intended that all matter contained in the foregoing description or shown in the accompanying drawings, shall be interpreted as illustrative and not in a limiting sense.

B. Magnetic Treatment Device for Cardiac Dysfunction Static Magnetic Stabilizer—(SMS-C).

The electromagnetic flux generator head and circuits of the invention are schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration.

As embodied herein and schematically represented in FIG. 2, magnetic flux generator 12 comprises four substantially identical electromagnetic bodies 18, 20, 22 and 24 on a containment structure. Containment structure may comprise a mounting board, a flux return ring (made of a ferroconductor), a casing or any other structure that will hold electromagnetic bodies 18, 20, 22 and 24 in the desired configuration. The structure must then be held in place for proper alignment of the fields to best cover the area of the myocardium as shown in FIG. 5. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane, and are oriented in a quadrilateral configuration with positive poles oriented diagonally opposite one another and negative poles oriented diagonally opposite one another. Electromagnetic bodies 18, 20, 22 and 24 preferably comprise electromagnetic heads as best shown in FIGS. 2, 3 and 5. Each electromagnetic head includes a conducting wire 26 wound around a cast iron case 28. Wire 26 may be comprised of any conducting material, as for example copper or aluminum. For example, FIG. 3 shows a suitable electromagnet made using a five inch (12.7 cm) outer diameter with a two inch (5.08 cm) center core 28 and a one and one-half inch (3.81 cm) coil space with 3200 turns of #22 copper wire. As shown in FIG. 2, coils 19, 21, 23 and 25 of electromagnetic heads 18, 20, 22 and 24. Respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. Attached to the containment means are three (3) important and function altering components of the technology. Flux return ring 16a is attached to the bottom of the described 4 electromagnetic heads, this ring enhances the flux field and controls unwanted stray induction currents as well as stray flux from the opposite pole. A flux focusing ring 16 is positioned around the flux heads adjacent to the insulated wire coils, it being about 2.5 inches wide (6.35 cm) and ¼ to ½ inches (6.35 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45° to 90° angle to the long axis of the primary flux pole. In this position, the flux focusing coils along with the focusing ring, the flux return ring and the new iron core of this invention make the gradient steeper, increase the field strength and decrease healing and stray high currents. The flux return ring and the flux focusing ring are grounded to reduce stray induction currents and the variables that they add to the therapeutic magnetic field.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current to power source 38 be a 120 volt AC source. It is preferred that the direct current generator 36 be capable of producing a 30 amp, 120 volt DC current. It is further preferred that capacitor 51 be capable of storing 8000 volts of DC current when switches 53 are closed as in FIG. 4. An additional requirement of the invention is that pulse discharge switch 52 capable of closing the discharge circuit through poles b and c when said switch is depressed thereby discharging the capacitor voltage into the flux generator 12, thereby depolarizing the myocardium and defibrillating the heart as a consequence. When said switch 52 is depressed, switch pole a. is open therefore breaking the circuit through a–b. It is a further requirement of the invention that when discharge switch 52 is not depressed, circuit through poles a–b is closed. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Rheostat 50 is preferably embodied as any conventional rheostat having a 50 amp, 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the flux generator head, may be individually regulated such that symmetric magnetic power may be balanced among all heads. It is anticipated that each magnetic treatment head could alternatively be individually connected to one of four rheostats in control unit 34 such that electric current supplied to each of the four individual treatment heads or poles could be individually regulated by a computer driven servomechanism.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

Figure 8:
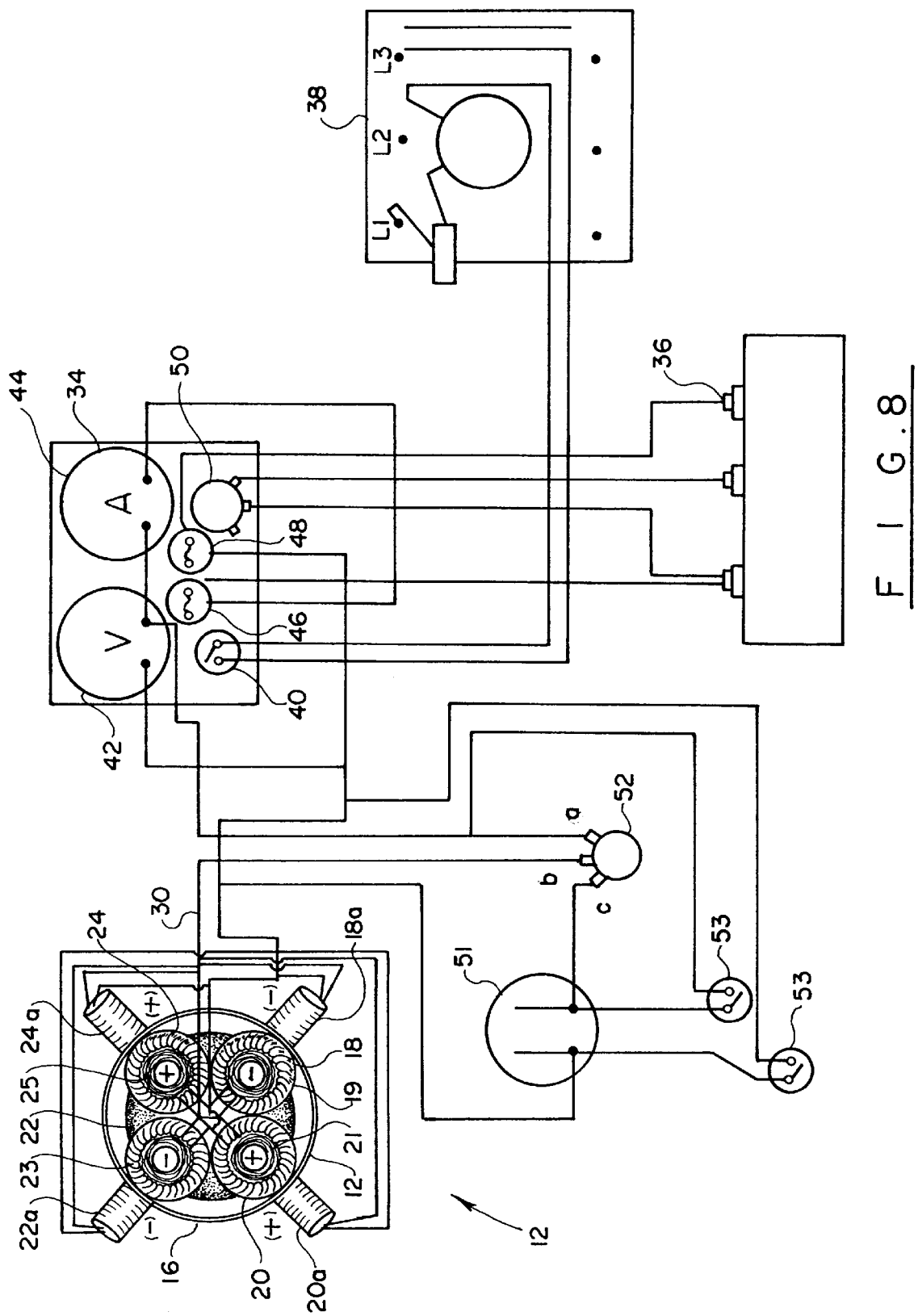
FIG. 8 is a schematic diagram showing electrical connections between the components of the electromagnetic treatment device of the invention along with the defibrillation unit.

According to the invention, the therapeutic electromagnetic treatment device of the invention may be mounted on a support structure adapted to align the four electromagnets against the body of a living animal. As embodied herein, the support structure may comprise treatment table, bed or other similar assembly. FIG. 5 shown an elongated treatment table support structure 62 having a magnetic flux generator 12 of the invention affixed to the bottom surface thereof. A similar embodiment of the invention is affixed to a hospital intensive care unit bed as an alternative embodiment of the present invention. Flux generator 12 is preferably powered by a power source as described in FIG. 8 (not shown) as previously described. Flux generator 12 moves laterally along the bottom surface of table 62 on rails 64 and 65. Flux generator 12 may be moved manually or by a power driven actuating mechanism 58 such that flux generator 12 may be aligned with a desired portion of a human body to which the pulsed or steady state magnetic flux is to be applied. A magnetic flux field is generated by each of the electromagnetic heads on flux generator 12 when the electromagnetic heads are energized. A magnetic flux field so generated by the electromagnetic heads extends above a top planar surface 60 of table 62 such that magnetic flux impinges upon a body on the table surface and exerts very steep three dimensional field gradient upon the organ under treatment.

The therapeutic electromagnetic treatment device of the invention may be otherwise supported by a number of different support means to allow for portability.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the flux generator head is supported by support means such that the quadripolar flux may be applied to the body area of the myocardium in varying intensity from a steady state to a high voltage pulse capacitor discharge. This discharge being applied to defibrillate the myocardium and to prevent recurrent fibrillation, pain and coronary artery spasms.

In A preferred embodiment, the four magnetic poles of the flux generator head of the therapeutic electromagnetic treatment device include two positive poles defining opposite diagonal vertices and the two negative poles defining opposite diagonal vertices of the quadrilateral shape, each of the magnetic poles being oppositely charged poles and being magnetically repelled by the like charged pole.

Further, the plurality of electromagnetic bodies of the therapeutic electromagnetic treatment device can comprise four substantially identical electromagnets, two of the electromagnets having a positive magnetic pole in the substantially single plane and two of the electromagnets having a negative magnetic pole in the substantially single plane, each of the four electromagnets generating a magnetic flux field when energized by the power means.

Additionally, the four electromagnets of the therapeutic electromagnetic treatment device can each comprise a cast iron core wound with electrically conducting wire; additionally, the wire can be a copper wire or an aluminum wire.

In a preferred embodiment of the therapeutic electromagnetic treatment device, the quadrilateral shape is a parallelogram shape, or a rectangle shape, or a square shape.

Further, the power means for therapeutic electromagnetic treatment device may comprise a direct current generator and said power means electrically connected to each of the four electromagnets of a single flux generator head.

Another embodiment of the therapeutic electromagnetic treatment device may further comprise power control means for controlling the amount of electrical power supplied to each of the four electromagnets so as to regulate the magnetic flux field generated by each of the four electromagnets in the magnetic flux generator head.

The containment means of the therapeutic electromagnetic treatment device may further be mounted on a support structure adapted to align the four electromagnetic flux generator heads in the appropriate orientation within the treatment structure such that the myocardium may properly receive the desired flux field.

Further, the support structure of the therapeutic electromagnetic treatment device may comprise an attachment devise for support of the magnetic flux generator head within an intensive care unit bed within a hospital, the hospital bed being for supporting the body of a living animal, the magnetic flux field generated by the four electromagnets of the flux generator head exposes the human or animal to about 200 milli Tesla of energy and steep three dimensional field gradients, when the electromagnets are energized by the power means.

Additionally, in a further embodiment of the instant invention, a method of therapeutically placing an electromagnetic treatment device in proximity of the chest and myocardium to control pathological processes which accompany a myocardial infarction such as arrhythmia, chest pain and decreased myocardial blood flow, may comprise the steps of: assembling at least one group of electromagnetic bodies having in each group at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body at a position facing the chest of a human posteriorly, thereby exposing the myocardium to a steep field gradient penetrating the heart of a human or animal; and energizing the magnetic bodies with electric power so that each of the magnetic bodies generate a magnetic flux field.

A further embodiment of the instant invention involves a method of therapeutically placing an electromagnetic treatment device in proximity of the heart of an animal to control the pathophysiology of a heart undergoing a myocardial infarction, comprising the steps of: assembling at least one group of electromagnetic bodies having at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing each orientation of the plurality of magnetic bodies in a single containment body; selectively placing containment body at a position in relation to the heart of a human or animal to treat the complications of myocardial infarction; and energizing the magnetic bodies with electric power so that each of the magnetic bodies generate a magnetic flux field.

C. Magnetic Treatment Device for the Control of Drug Resistant Seizures and Cerebral Edema—Static Magnetic Stabilizer (SMS-E).

One of two identical electromagnetic heads and circuits of the invention is schematically illustrated in FIG. 1. Treatment device 10 include a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration. Attached to the containment means are three (3) important and function altering components of the technology. Flux return ring 16a is attached to the bottom of the described 4 electromagnetic heads, this ring enhances the flux field and controls unwanted stray induction currents as well as stray flux from the opposite pole. A flux focusing ring 16 is positioned around the flux heads adjacent to the insulated vire coils, it being about 2.5 inches wide (6.35 cm) and ¼ to ½ inches (6.35 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45° to 90° angle to the long axis of the primary flux pole. In this position, the flux focusing coils along with the focusing ring, the flux return ring and the new iron core of this invention make the gradient steeper, increase the field strength and decrease healing and stray high currents. The flux return ring and the flux focusing ring are grounded to reduce stray induction currents and the variables that they add to the therapeutic magnetic field.

Figure 9:
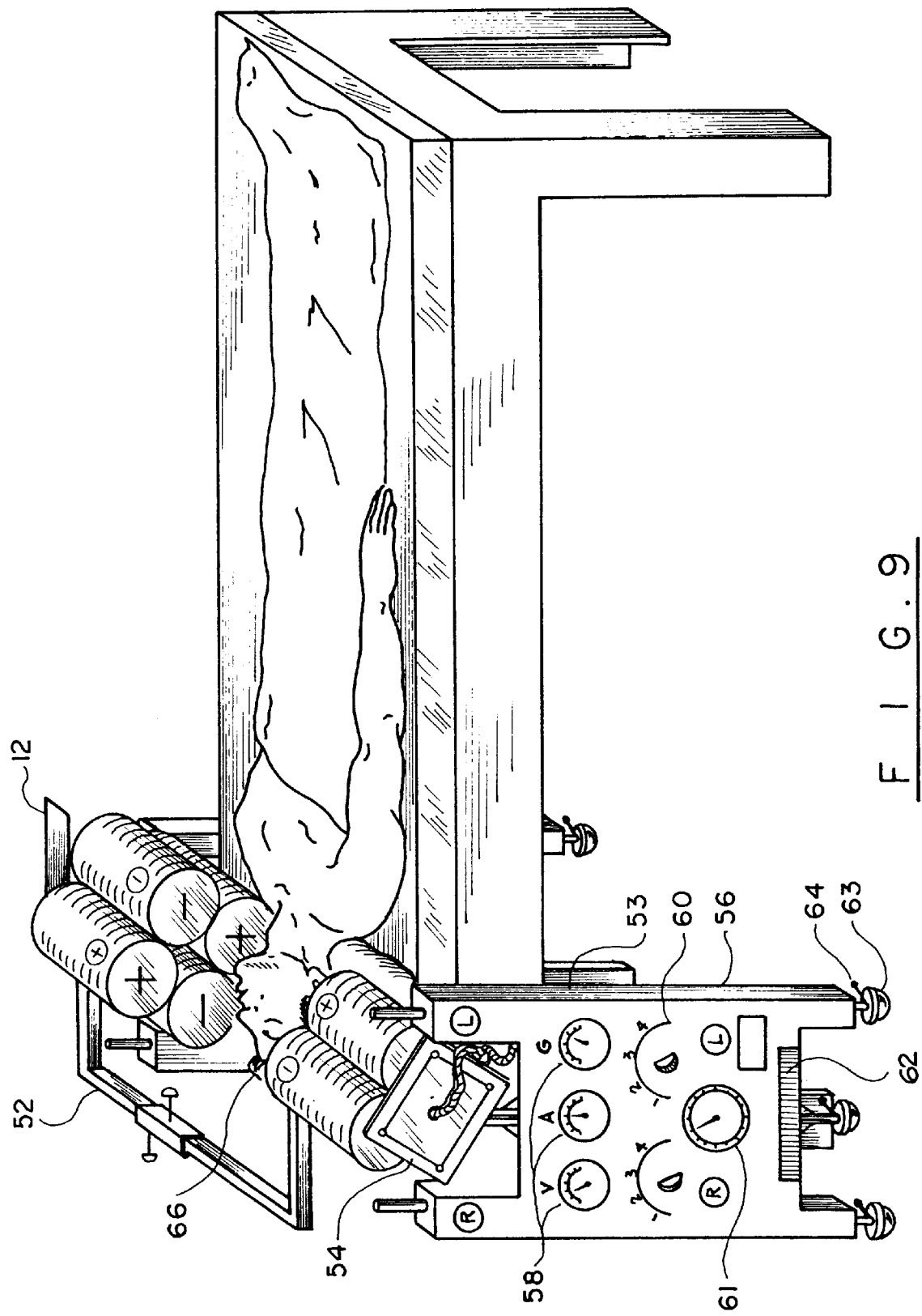
FIG. 9 is a perspective view of a preferred embodiment of the electromagnetic treatment device of the invention.

As embodied herein, magnetic flux generator 12 comprises four substantially identical Electromagnetic bodies 18, 20, 22 and 24 on a containment structure. The containment structure may comprise a mounting board, a flux return ring (made of a ferroconductor), a casing or any other structure that will hold electromagnetic bodies 18, 20, 22 and 24 in the desired configuration. The structure must then be held in place for proper alignment of the attracting fields of the two heads of the invention as shown in FIG. 9. In the preferred embodiment, electromagnetic bodies 18 and 22 each form a negative magnetic pole while electromagnetic bodies 20 and 24 each form a positive magnetic role. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 preferably comprise electromagnetic heads as best shown in FIGS. 2, 3 and 9. Each electromagnetic head includes a conducting wire 26 wound around a cast iron case 28. Wire 26 may be comprised of any conducting material, as for example copper or aluminum For example, FIG. 3 shows a suitable electromagnet made using a five inch (12.7 cm) outer diameter with a two inch center core 28 and a one and one-half inch (3.81 cm) c oil space with 3200 turns of #22 copper wire. As shown in FIG. 2 coils 19, 21, 23 and 25 of electromagnetic heads 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time.

Rheostat 50 is preferably embodied as any conventional rheostat having a 50 amp, 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated. These rheostats could also be held to constant stable magnetic flux by driving the rheostats by a servo-control driven by a computer. The computer would maintain the heads in perfect balance and therefore allow the best possible biological effect, when reduced to practice.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field or some combination thereof.

According to the invention, the therapeutic electromagnetic treatment device of the invention may be mounted on a support structure adapted to align the four electromagnets such that they may be aligned with the other head such that the heads are facing each other with the center axis of each electromagnet meeting in the center with opposite poles facing. This configuration increases the peak power of each pole and makes the gradient steeper. The increased peak power and increased slope of the gradient both improve the biological effect. FIG. 5 shows the means to support the two heads and to fasten them together. The two heads are magnetic flux generators. Flux generator 12 is preferably powered by a power source (not shown) like that described above. The flux generators 12 move in the x, y and z axis in order to get appropriate peak magnetic flux and peak magnetic gradient. Flux generators 12 may be moved manually or by a power driven actuating mechanism 54 such that flux generators 12 may be aligned with the desired position of a human or animal head and upper spine to which magnetic flux is to be applied. A magnetic flux field is generated by each of the electromagnetic poles on flux generator 12 when the electromagnetic poles are energized. A magnetic flux field so generated by the electromagnetic heads extends laterally from a planar surface such that the magnetic flux impinges upon an area of the head and/or upper cervical spine of the body positioned between the two flux generators 12. The flux field is managed and manipulated by the flux return and flux focusing ring which hold focusing magnets.

The support means 56 allows both the left and right side sections to be rolled into place forward and locked together by lock bars 52 and 53. Lock bar 53 is underneath the bed. Support means 56 contains the DC power source 14 and provides support for the quadripolar flux generators 12. The support means 56 also contains control meters 58, pole selectors 60 and voltage regulator (DC) 61. A lead counter weight 62 functions to counter balance the flux generators 12. The caster rollers 63 provide the ability to move support means 56 to the bedside.

The patient's head 66 is placed in the static quadripolar field between the two flux generators 12.

The electromagnetic treatment device of this invention has been beneficially applied to the body and head of laboratory animals and humans to control seizures of the brain and to retard and/or reverse brain swelling (cerebral edema). Laboratory data supporting utility is presented below.

Laboratory Data

The beneficial effects of the electromagnetic treatment device of the present invention, at least in part are brought about by the quadripolar, alternating, center charged, symmetric, static magnetic field (maximized by the flux return, flux focusing ring and focusing magnets) impinging upon the cell walls of cells in the brain of animals and man. The steep gradient of these fields brings about a polarization of the lipoprotein matrix of the cell walls such that sodium and calcium channels are blocked in such a fashion as to impede the flux of these ions. Impedance of ion flux blocks the uncontrolled depolarization of brain neurons, thereby preventing the spread of electrical activity which is generated by a seizure focus. Impedance of ion flux also blocks the pacemaker effect of the seizure focus (i.e. blocks initiation of a spontaneous depolarization). The control of spontaneous depolarization of brain neurons brings about control of a seizure focus and control of spread of the erratic depolarization of adjacent neurons. Stabilization of cell walls also inhibits extracellular fluid migration and therefore controls edema of the brain and subsequent cell death.

It will be apparent to those skilled in the art that modifications and variations can be made in the electromagnetic treatment device and method for applying the electromagnetic treatment device of the present invention. The invention in its broader aspects, therefore is not limited to the specific details, representative methods and apparatus and illustrative examples shown and described above. Thus, it is intended that all matter contained in the foregoing description as shown in the accompanying drawings shall be interpreted as illustrative and not in a limiting sense.

Invention Design-Support Data

The purpose of this data is to support the design of this invention. The biological effect of this invention is dependent upon the field gradient and the field intensity. The gradient arid the intensity may both be increased by approaching one of the flux generator heads of the invention with a second flux generator head with the facing poles being oppositely charged. FIG. 6 demonstrates the change in slope of line d as the peak flux intensity is increased as in sloped line e. The evidence to support the claim of increased energy or peak energy which results from an attracting flux generator is noted in table #1 (See FIG. 4 flux generator 12, Poles A, B, C, D).

TABLE I

| Reading in Millitesla | A | B | C | D |
|---|---|---|---|---|
| Generator #1 | +73 | −67 | +72 | −72 |
| Generator #1 + Generator #2 2.9 inches (7.4 cm) from #1 | +94 | −92 | +87 | −84 |
| Generatire #1 + Generator #2 | +81.4 | −75 | +79 | −80 |

TABLE I-continued

| Reading in Millitesla | A | B | C | D |
|---|---|---|---|---|
| 2.9 inches (7.4 cm) from #1 | | | | |
| Generator #1 + Generator #2 4.2 inches (10.7 cm) from #1 | +78 | −72 | +75 | −75 |

Table 1. Table #1 is a summation of the flux density in the center of each pole of the flux generator #1: a) In isolation b) when flux generator #2 is faced toward #1 with the poles in an attracting position at varying distances from Generator #1. It is noted the peak flux is increased when a pole is approached by an opposite and attracting pole. As can be noted in FIG. #6, this effect of increasing the strength of the field simultaneously increases the gradient.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein two flux generator heads are supported by support means such that the planar surface faces poles of each face in the attracting mode when two flux heads are energized.

Further, the four magnetic poles of each flux generator of the therapeutic electromagnetic treatment device may include two positive poles defining opposite diagonal vertices and the two negative poles defining opposite diagonal vertices of the quadrilateral shape, each of the magnetic poles being oppositely charged poles and being magnetically repelled by said like charged pole.

In a further embodiment of the instant invention, the plurality of electromagnetic bodies of the therapeutic electromagnetic treatment device may comprise four substantially identical electromagnets, two of the electromagnets having a positive magnetic pole in the substantially single plane and two of the electromagnets having a negative magnetic pole in the substantially single plane, each of the four electromagnets generating a magnetic flux field when energized by the power means.

The four electromagnets of the therapeutic electromagnetic treatment device may each comprise a cast iron core wound with electrically conducting wire, which can be copper wire or aluminum wire.

Further, the quadrilateral shape of the therapeutic electromagnetic treatment device can be a parallelogram shape, a rectangle shape, or a square shape.

Further, the power means of the therapeutic electromagnetic treatment may comprise a direct current generator and the power means may be electrically connected to each of the four electromagnets of a single flux generator head.

Further still, the therapeutic electromagnetic treatment device of the invention may further comprise a power control devise for controlling the amount of electrical power supplied to each of the four electromagnets so as to regulate the magnetic flux field generated by each of the four electromagnets in both magnetic flux generator heads.

Additionally, the containment means of the therapeutic electromagnetic treatment device can be mounted on a support structure adapted to align the four electromagnets of the magnetic flux generator head in the same orientation as the second magnetic flux generator head such that the two heads are facing and in a parallel position.

The support structure of the therapeutic electromagnetic treatment device may further comprise a cabinet for the support of each magnetic flux generator head, the support structure being mounted on coasters for easy mobility and having a means to fasten the two flux generator heads together once they are in position over the bed or table, the bed being for supporting the body of a living animal in which the head and cervical area is placed between the two flux generator heads, the magnetic flux field generated by each of the four electromagnets of each flux generator head exposes the human or animal head to 50 up to 500 milli Tesla of energy and steep three dimensional field gradients, when the electromagnets are energized by the power means.

A further embodiment of the instant invention involves a method of therapeutically placing a electromagnetic treatment device in proximity of the head and cervical spine of an animal to control seizure discharges and cerebral edema, comprising the steps of: assembling at least two groups of electromagnetic bodies having in each group at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of plurality of magnetic bodies in a single containment body; selectively placing the containment body at a position facing the second containment body with the quadripolar, steep gradient field penetrating the brain of a seizing animal; and energizing the magnetic bodies with electric power so that each of the magnetic bodies generate a magnetic flux field.

D. Magnetic Treatment Device for Control of Pain and Edema—Sustained in Severe Burns—Static Magnetic Stabilizer (SMS-B)

One of the electromagnetic heads and circuits of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration.

Figure 10:
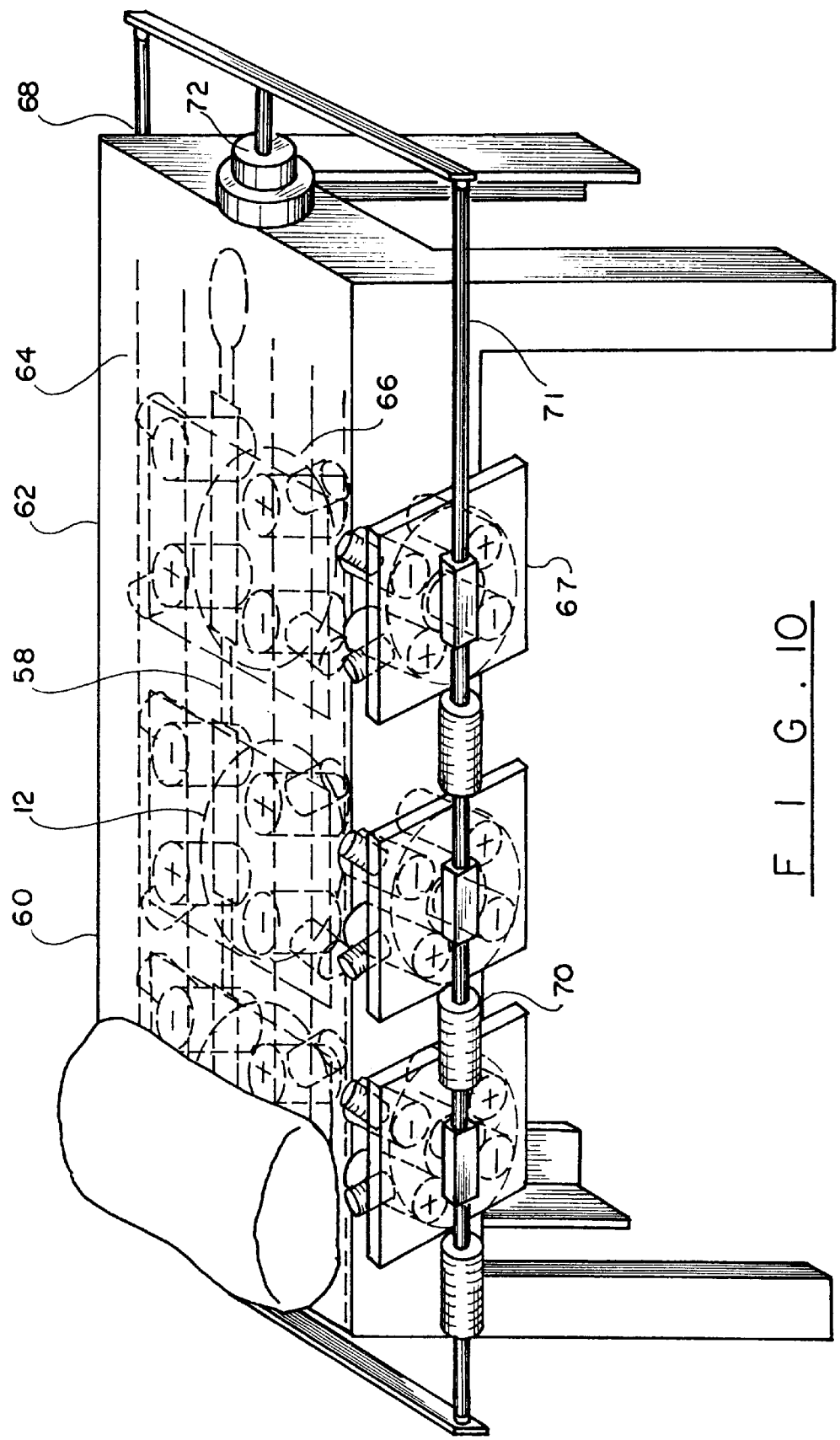
FIG. 10 is a perspective view of a preferred embodiment of the electromagnetic treatment device of the invention.

As embodied herein, magnetic flux generator 12 comprises four substantially identical electromagnetic bodies 18, 20, 22 and 24 on a containment structure 16. Containment structure 16 may comprise a mounting board, a flux return ring (made of a ferroconductor), a casing or any other structure that will hold electromagnetic bodies 18, 20, 22 and 24 in the desired configuration. The structure must then be held in place for proper alignment to deliver the magnetic flux of the invention as shown in FIG. 10. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 preferably comprise electromagnetic heads as best shown in FIGS. 2, 3 and 10. Each electromagnetic head includes a conducting wire 26 wound around a cast iron case 28. Wire 26 may be comprised of any conducting material, as for example copper or aluminum. For example, FIG. 3 shows a suitable electromagnet made using a five inch (12.7 cm) outer diameter and with a two inch (5.08 cm) center core 28 and a one and one-half inch (3.81 cm) coil space with 3200 turns of #22 copper wire. As shown in FIG. 2, coils 19, 21, 23 and 25 of electromagnetic heads 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. Attached to the containment means are three (3) important and function altering components of the technology. Flux return ring 16a is attached to the bottom of the described 4 electromagnetic heads, this ring enhances the flux field and controls unwanted stray induction currents as well as stray flux from the opposite pole. A flux focusing ring 16 is positioned around the flux heads adjacent to the insulated wire coils, it being about 2.5 inches wide (6.35 cm) and ¼ to ½ inches (6.35 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45° to 90° angle to the long axis of the primary flux pole. In this position, the flux focusing coils along with the focusing ring, the flux return ring and the new iron core of this invention make the gradient steeper, increase the field strength and decrease healing and stray high currents. The flux return ring and the flux focusing ring are grounded to reduce stray induction currents and the variables that they add to the therapeutic magnetic field.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Rheostat 50 is preferably embodied as any conventional rheostat having a 50 amp, 120 volt capacity. As shown in FIG. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated. These rheostats could also be held to constant stable magnetic flux by driving the rheostats by a servo control driven by a computer. The computer would maintain the heads in perfect balance, therefore allowing the best possible biological effect.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite film the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

According to the invention, the therapeutic electromagnetic treatment devices of the invention may be mounted on support structures adapted to align the four electromagnets against the body of a living animal which has sustained major burn injury. As embodied herein, the support structure may comprise treatment table, bed or other similar assembly. FIG. 5 shows an elongated treatment table support structure 62 having a magnetic flux generator 12 of the invention affixed to the bottom surface and two movable arms thereof. According to the invention, each bank of flux generator heads (12) is constituted of 3 flux generator heads in each bank of generator heads. A similar embodiment of the invention is affixed to a hospital burn unit bed as an alternative embodiment of the present invention. Flux generator 12 is preferably powered by a power source as described in FIG. 4 (not shown) as previously described. Flux generator 12 as contained in the bottom of the bed, moves laterally along the bottom surface of table 62 or rails 64 and 66. Flux generator 12 is moved by a power driven actuating mechanism 58 such that flux generator 12 may be aligned with a desired portion of a human body to which the steady state magnetic flux is to be applied. A magnetic flux field is generated by each of the electromagnetic heads on flux generator 12 when the electromagnetic heads are energized. A magnetic flux field so generated by the electromagnetic heads counter balance support arms (71). Each flux generator head 12 is controlled by a servomotor mechanism 70 which is designed to maintain the focus of the flux field gradient as the counter support arms are rotate up to 30° to 45° above the top planar surface 60 of the table 62 such that magnetic flux impinges upon a body upon the table surface and exerts a very steep three dimensional field gradient upon the burn damaged tissue under treatment. The counter balance support arms 71 are rotated every 10 minute s by servomotor and gear 72. When magnetic flux generator heads 67 or 68 clear the surface 60 of table 62, magnetic flux generator heads 12in the bottom of the table or bed are turned off by a microswitch in motor and gear 72. When electromagnetic flux generator bank 67 and 68 drop below the surface 60 of table 62, the microswitch turns the electromagnetic flux generator bank in the bottom of the on position such that the electromagnetic flux heads are charged with DC current and produce a static field steep gradient flux field which again impinges upon the body. When magnetic flux generator bank in the bottom of the table or bed is in the off position, the flux generators 67 and 68 are in the on position and are producing the desired magnetic flux field with a steep 3 dimensional gradient.

The therapeutic electromagnetic treatment device of the invention may be otherwise structured without violating the basic mechanism of function.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the flux generator heads are supported by support devices such that the quadripolar flux may be applied to the body area of severe burn in varying intensity, the discharge being applied to burn damaged tissue to reduce pain, edema and speed healing.

In a further embodiment of the instant invention, the four magnetic poles of the flux generator head of the therapeutic electromagnetic treatment device include two positive poles defining opposite diagonal vertices and the two negative poles defining opposite diagonal vertices of the quadrilateral shape, each of the magnetic poles being oppositely charged poles and being magnetically repelled by the like charged pole.

Further, the plurality of electromagnetic bodies of the therapeutic electromagnetic treatment device may comprise four substantially identical electromagnets, two of the electromagnets having a positive magnetic pole in the substantially single plane and two of the electromagnets having a negative magnetic pole in the substantially single plane, each of the four electromagnets generating a magnetic flux field when energized by the power means.

Additionally, the four electromagnets of the therapeutic electromagnetic treatment device can each comprise a cast iron core wound with electrically conducting wire, the wire further may be either is copper or aluminum wire.

Further still, the quadrilateral shape of the therapeutic electromagnetic treatment device may be a parallelogram shape, a rectangle shape, or a square shape.

In another embodiment of the instant invention, the power means of the therapeutic electromagnetic treatment device comprises a direct current generator and the power means is electrically connected to each of the four electromagnets of a single flux generator head.

Further, the therapeutic electromagnetic treatment device may further comprise a power control means for controlling the amount of electrical power supplied to each of the four electromagnets so as to regulate the magnetic flux field generated by each of the four electromagnets in each of the 9 magnetic flux generator heads.

Additionally, the containment means of the therapeutic electromagnetic treatment device can be mounted on a support structure such as a table and bed such that the electromagnetic flux generator heads in the appropriate orientation within the treatment structure such that the burned body may properly receive the desired flux field. The support structure may further comprise an attachment device for support of the magnetic flux generator heads within a burn unit bed within a hospital, the hospital bed being for supporting the body of a living animal, the magnetic flux field being generated by the four electromagnets of the flux generator heads exposes the human or animal to about 200 milli Tesla of energy and steep three dimensional field gradients, when the electromagnets are energized by the power means.

Another embodiment of the instant invention involves a method of therapeutically placing an electromagnetic treatment device in proximity of the human, or other animal, body to control pathological processes which accompany a serious burn, comprising the steps of: assembling at least one group of electromagnetic bodies having in each group at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body in a bank of magnetic flux generator heads, thereby exposing the body to a steep field gradient penetrating the body of a human or animal; and energizing the magnetic bodies with electric power so that each of the magnetic bodies generate a magnetic flux field.

Another embodiment of the present invention involves a method of therapeutically placing an electromagnetic treatment device in proximity of the body of an animal to control the pathophysiology of severe burns, comprising the steps of: assembling at least one group of electromagnetic bodies having at least two positive magnetic poles substantially in a single plane, having at least two negative magnetic poles substantially in a single plane; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing each orientation of the plurality of magnetic bodies in a single containment body; selectively placing containment body at a position in relation to the body of a human or animal to treat the complications of severe burns; and energizing the magnetic bodies with electric power so that each of magnetic bodies generate a magnetic flux field.

E. Magnetic Treatment Device for Potentiation of Pharmaceutical Agents (SMS-D).

Reference will now be made in detail to the presently preferred embodiments of the invention, examples of which are illustrated in the accompanying drawings. Throughout the drawings, like reference characters are used to designate like elements.

One of the two electromagnetic heads and circuits of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration. Attached to the containment means is three (3) important and functional components of the technology. Flux return ring 16a is attached to the bottom of the described 4 electromagnetic heads, this ring enhances the flux field and controls unwanted stray flux from the opposite pole. A flux focusing ring 16 is positioned around the flux heads, it being about 2.5 inches wide (6.35 cm) and ¼ to ½ inches (6.35 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45° to 90° angle to the long axis of the primary flux pole. In this position, the flux focusing coils along with the focusing ring will make the gradient steeper and increase the effective field strength. The flux return ring and the flux focusing ring are grounded to reduce stray induction currents and the variables that they add to the therapeutic magnetic field.

As embodied herein, magnetic flux generator 12 comprises four substantially identical electromagnetic bodies on a containment means. Containment means may comprise a mounting board, a flux return ring 16a (made of a ferroconductor), a casing or any other structure that will hold electromagnetic bodies 18, 20, 22 and 24 in the desired configuration. A flux field focusing ring 16 is attached to the outer surface of the coils 18, 20, 22 and 24; this focusing ring holds focusing electromagnetic poles 18a, 20a, 22a and 24a. The structure must then be held in place for proper alignment of the attracting fields of the two heads of the invention as shown in FIG. 11. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 with their flux return ring and focusing ring along with the focusing magnets comprise electromagnetic heads as best shown in FIGS. 2, 3 and 11.

Each electromagnetic head includes a conducting wire 26 wound around a cast iron case 28. Wire 26 may be comprised of any conducting material, as for example copper or aluminum. For example, FIG. 3 shows a suitable electromagnet made using a five inch (12.7 cm) outer diameter with a two inch (5.08 cm) center core 28 and a two inch (5.08 cm) coil space with 3200 turns of #22 copper wire. As shown in FIGS. 2 and 3, coils 19, 21, 23 and 25 of electromagnetic heads (shown in cut away) 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. FIG. 3 represents a cutaway view with insulation 29 being cut away to reveal wire coil 26.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Electromagnetic focusing magnets 18a, 20a, 22a and 24a may be on separate rheostats to better balance the field. Rheostat 50 is preferably embodied as any conventional rheostat having a 50 amp, 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

According to the invention, the therapeutic electromagnetic treatment device of the invention may be mounted on a support structure adapted to align the four electromagnets such that they may be aligned with the other head such that the heads are facing each other with the center axis of each electromagnet meeting in the center with opposite poles facing. This configuration increases the peak power of each pole and makes the gradient steeper. The increased peak power and increased slope of the gradient both improve the biological effect. FIG. 11 shows the means to support the two heads and fasten them together. The two heads are magnetic flux generators. Flux generator 12 is preferably powered by a power source (not shown) like that described above. The flux generators 12 move in the x, y and z axis in order to get appropriate peak magnetic flux and peak magnetic gradient. Flux generators 12 may be moved manually or by a power driven actuating mechanism 54 such that flux generators 12 may be aligned with the desired position of a human or animal head, upper spine or any other portion of the body to which magnetic flux is to be applied. A magnetic flux field is generated by each of the electromagnetic poles on flux generator 12 when the electromagnetic poles are energized. A magnetic flux field so generated by the electromagnetic heads extends laterally from a planar surface such that magnetic flux impinges upon an area of the head and/or upper cervical spine or other parts of the body positioned between the two flux generators 12. The flexible placement allows maximum use for potentiation of pharmaceuticals.

The support means 56 allows both the left and right side sections to be rolled into place forward and locked together by lock bars 52 and 53. Lock bar 53 is underneath the bed. Support means 56 contains the DC power source 14 and provides support for the quadripolar flux generators 12. The support means 56 also contains control meters 58, pole selectors 60 and voltage regulator (DC) 61. A lead counter weight 62 functions to counter balance the flux generators 12. The caster rollers 63 provide the ability to move support means 56 to the bedside.

The patient is placed in the static quadripolar field between the two flux generators 12.

The electromagnetic treatment device of this invention has been beneficially applied to the body and head of laboratory animals and humans to potentiate the therapeutic effect of pharmaceutical agents.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the two flux generator heads are supported by support means such that the planar surface faces poles of each face in the attracting mode when two flux heads are energized.

Further, the four magnetic poles of each flux generator of the therapeutic electromagnetic treatment device can include two positive poles defining opposite diagonal vertices and the two negative poles defining opposite diagonal vertices of the quadrilateral shape, each of the magnetic poles being oppositely charged poles and being magnetically repelled by the like charged pole. A flux return ring may be attached to the bottom of the described 4 electromagnetic heads, this ring enhances the flux field and controls unwanted stray electrical flux from the opposite pole. A flux focusing ring may further be positioned around the flux heads. An attachment device may hold the focusing ring in proper location for maximum benefit. Attached to the flux focusing ring may be focusing coils. These focusing electromagnetic coils are attached to the flux focusing ring in adjacent to the flux head of like charge and at a 45° to 90° angle to the long axis of the primary flux pole. In this position the flux focusing coils along with the focusing ring generate a steeper field gradient and increase the effective field strength.

The flux return ring and the flux focusing ring may further be grounded to reduce the stray induction currents and the variables that they add to the therapeutic magnetic field.

Additionally, the 4 electromagnetic poles, with flux return ring, focusing ring and focusing coils may be referred to as the "Therapeutic Head."

In another embodiment of the present invention, the plurality of electromagnetic bodies of the therapeutic electromagnetic treatment may comprise four substantially identical electromagnet flux heads, two of the electromagnets having a positive magnetic pole in the substantially single plane and two of the electromagnets having a negative magnetic pole in the substantially single plane, each of the four electromagnets generating a magnetic flux field when energized by the power means.

Further, the four electromagnets of the therapeutic electromagnetic treatment device may each comprise a cast iron core wound with electrically conducting wire which can be a copper wire or an aluminum wire.

Further still, the quadrilateral shape for the therapeutic electromagnetic treatment device can be a parallelogram shape or, inter alia, a rectangle or square shape.

In still a further embodiment of the present invention, the power means of the therapeutic electromagnetic treatment device may comprise a direct current generator and the power means may be electrically connected to each of the four electromagnets of a single flux generator head along with connection to the flux focusing magnets. Additionally, the power control means can be adjustable for controlling the amount of electrical power supplied to each of the four electromagnets so as to regulate the magnetic flux field generated by each of the four electromagnets in both magnetic flux generator heads.

Also the containment means of the electromagnetic treatment device may be mounted on a support structure adapted to align the four electromagnets of the magnetic flux generator head in the same orientation as the second magnetic flux generator head such that the two heads are facing and in a parallel position. In addition, the support structure may further comprise a cabinet for the support of each magnetic flux generator head, the support structure being mounted on coasters for easy mobility and having means to fasten the two flux generator heads together once they are in position over the bed or table, the bed being for supporting the body of a living animal in which the head, cervical area or other parts of the body are placed between the two flux generator heads, the magnetic flux field generated by each of the four electromagnets of each flux generator head exposes the human or animal head to 50 up to 500 milli Tesla of energy and steep three dimensional field gradients which can be manipulated by the flux return ring, flux focusing ring on flux focusing heads, when the electromagnets are energized by the power means.

Another embodiment of the present invention involves a method of therapeutically placing an electromagnetic treatment Therapeutic Head in proximity of the head, cervical spine or other body areas potentiate the effects of pharmaceuticals, comprising the steps of: assembling at least two groups of electromagnetic bodies having in each group at least two positive magnetic poles substantially in a single plane, having at least two negative magnetic poles substantially in a single plane, along with a flux return ring, flux focusing ring and focusing magnets; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body at a position facing the second containment body with the quadripolar, steep gradient field penetrating the body of the animal; and energizing the magnetic bodies with electric power so that each of the magnetic bodies generate a magnetic flux field.

Another embodiment of the present invention involves a method of therapeutically placing an electromagnetic treatment device in proximity of the body of an animal to potentiate the effectiveness of pharmaceuticals, comprising the steps of: assembling at least two groups of electromagnetic bodies having at least, in each body, two positive magnetic poles substantially in a single plane, having at least two negative magnetic poles substantially in a single plane along with a flux return ring, focusing ring and focusing electromagnets attached to the focusing ring; orienting the two positive poles and the two negative poles of said plurality of magnetic bodies in a single plane to define the four vertices of a rectangle shape with the two positive poles defining opposite diagonal vertices and the two negative poles defining opposite vertices of the rectangular shape; fixing each said orientation of the plurality of magnetic bodies in a single containment body; selectively placing containment bodies at a position in relation to the animal body part to treat the animal for potentiation of drugs; energizing the magnetic bodies with DC electric power so that each of the magnetic bodies generate a magnetic flux field.

F. Magnetic Treatment Device for Treatment of Strokes— For Protection from Cell Death Following Hypoxic Injury (SMS-S).

Reference will now be made in detail to the presently preferred embodiments of the invention, examples of which are illustrated in the accompanying drawings. Throughout the drawings, like reference characters are used to designate like elements.

One of the two electromagnetic heads and circuits of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration. Attached to the containment means are three (3) important and functional components of the technology. Flux return ring 16 is attached to the bottom of the described 4 electromagnetic heads, this ring enhances the flux field and controls unwanted stray flux from the opposite pole. A flux focusing ring 16 is positioned around the flux heads, it being about 2.5 inches wide (6.35 cm) and ¼ to ½ inches (6.3 5 mm–12.7 mm) thick. Attachment means hold the focusing ring in proper location for maximum benefit. Attached to the flux focusing ring are focusing coils 18a, 20a, 22a and 24a. Theses focusing coils are attached to the flux focusing ring in proximity to a head of like charge and at a 45° to 90° angle to the long axis of the primary flux pole. In this position, the flux focusing coils along with the focusing ring will make the gradient steeper and increase the effective field strength. The flux return ring and the flux focusing ring are grounded to reduce stray, induction currents and the variables that they add to the therapeutic magnetic field.

As embodied herein, magnetic flux generator 12 comprises four substantially identical electromagnetic bodies on a containment means. Containment means may comprise a mounting board, a flux return ring 16a (made of a ferroconductor), a casing or any other structure that will hold electromagnetic bodies 18, 20, 22 and 24 in the desired configuration. A flux field focusing ring 16 is attached to the outer surface of the coils 18, 20, 22 and 24; this focusing ring holds focusing electromagnetic poles 18a, 20a, 22a and 24a. The structure must then be held in place for proper alignment of the attracting fields of the two heads of the invention as shown in FIG. 9. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 with their flux return ring and focusing ring along with the focusing magnets comprise electromagnetic heads as best shown in FIGS. 2, 3 and 9.

Each electromagnetic head includes a conducting wire 26 wound around a cast iron core 28. Wire 26 may be comprised of any conducting material, as for example, copper or aluminum. For example, FIG. 3 shows a suitable electromagnet made using a five inch (12.7 cm) outer diameter wire coil with a two inch (5.08 cm) center iron core 28 and a two inch (5.08 cm) coil space with 3200 turns of #22 copper wire. As shown in FIGS. 2 and 3, coils 19, 21, 23 and 25 of electromagnetic heads (shown in cut away) 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. FIG. 3 represents a cut away view with insulation 29 being cut away to reveal wire coil 26.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes and on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Electromagnetic focusing magnets 18a, 20a, 22a and 24a may be on separate rheostats to better balance the field. Rheostat 50 is preferable embodied as any conventional rheostat having a 50 amp 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head, may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

According to the invention, the therapeutic electromagnetic treatment device of the invention may be mounted on a support structure adapted to align the four electromagnets such that they may be aligned with the other head such that the heads are facing each other with the center axis of each electromagnet meeting in the center with opposite poles facing. This configuration increases the peak power of each pole and makes the gradient steeper. The increased peak power and increased slope of the gradient both improve the biological effect. FIG. 9 shown the means to support the two heads and to fasten them together. The two heads are magnetic flux generators. Flux generator 12 is preferably powered by a power source (not shown) like that described above. The flux generators 12 move in the x, y and z axis in order to get appropriate peak magnetic flux and peak magnetic gradient. Flux generators 12 may be moved manually or by a power driven actuating mechanism 54 such that flux generators 12 may be aligned with the desired position of a human or animal head or spine or any other portion of the body to which magnetic flux is to be applied. A magnetic flux field is generated by each of the electromagnetic poles on flux generator 12 when the electromagnetic poles are energized. A magnetic flux field so generated by the electromagnetic heads extends laterally from a planar surface such that magnetic flux impinges upon an area of the head and/or upper cervical spine or other parts of the body positioned between the two flux generators 12.

The support means 56 allows both the left and right side sections to be rolled into place forward and locked together by lock bars 52 and 53. Lock bar 53 is underneath the bed. Support means 56 contains the DC power source 14 and provides support for the quadripolar flux generators 12. The support means 56 also contains control meters 58, pole selectors 60 and voltage regulator (DC) 61. A lead counter weight 62 functions to counter balance the flux generators 12. The caster rollers 63 provide the ability to move support means 56 to the bedside.

The patient is placed in the static quadripolar field between the two flux generators 12.

The electromagnetic treatment device of the invention has been beneficially applied to the body and head of laboratory animals to prevent cell death from hypoxia and/or noxious excitatory neurotransmitters.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the two flux generator heads are supported by support means such that the planar surface faces poles of each face in the attracting mode when two flux heads are energized.

Further, the four magnetic poles of each flux generator of the therapeutic electromagnetic treatment device may include two positive poles defining opposite diagonal vertices and the two negative poles defining opposite diagonal vertices of the quadrilateral shape, each of the magnetic poles being oppositely charged poles and being magnetically repelled by said like charged pole. A flux return ring may also be attached to the bottom of the described 4 electromagnetic heads, this ring enhancing the flux field and controls unwanted stray electrical flux from the opposite pole. Further, a flux focusing ring may be positioned around the flux heads, with an attachment means hold the focusing ring in proper location for maximum benefit. Attached to the flux focusing ring are focusing coils. These focusing electromagnetic coils are attached to the flux focusing ring in adjacent to the flux head of like charge and at a 45° to 90° angle to the long axis of the primary flux pole. In this position the flux focusing coils along with the focusing ring generate a steeper field gradient and increases the effective field strength. The flux return ring and the flux focusing ring may further be grounded to reduce the stray induction currents and the variables that they add to the therapeutic magnetic field. Additionally, the 4 electromagnetic poles, with flux return ring, focusing ring and focusing coils may be referred to as the "Therapeutic Head."

In another embodiment of the preferred invention, the plurality of electromagnetic bodies of the therapeutic electromagnetic treatment device may comprise four substantially identical electromagnet flux heads, two of the electromagnets having a positive magnetic pole in the substantially single plane and two of the electromagnets having a negative magnetic pole in the substantially single plane, each of the four electromagnets generating a magnetic flux field when energized by the power means.

Additionally, the four electromagnets of the therapeutic electromagnetic treatment device may each comprise a cast iron core wound with electrically conducting wire, and the wire may be, inter alia, a copper or aluminum wire.

Also in an embodiment of the present invention, quadrilateral shape may be, inter alia, a parallelogram, a rectangle shape or a square shape.

Also, the power means of the therapeutic electromagnetic treatment device may comprise a direct current generator and may be electrically connected to each of the four electromagnets of a single flux generator head along with connection to the flux focusing magnets. The power means may further comprise a power control means for controlling the amount of electrical power supplied to each of the four electromagnets so as to regulate the magnetic flux field generated by each of the four electromagnets in both magnetic flux generator heads.

Additionally the containment means or the therapeutic electromagnetic treatment device may be mounted on a support structure adapted to align said four electromagnets of the magnetic flux generator head in the same orientation as the second magnetic flux generator head such that the two heads are facing and in a parallel position. Further, the support structure may comprise a cabinet for the support of each magnetic flux generator head, the support structure being mounted on coasters for easy mobility and having a means to fasten the two flux generator heads together once they are in position over the bed or table, the bed being for supporting the body of a living animal in which the head and cervical area are placed between the two flux generator heads, the magnetic flux field generated by each of the four electromagnets of each flux generator head exposes the human or animal head to 50 up to 500 milli Tesla of energy and steep three dimensional field gradients which can be manipulated by the flux return ring, flux focusing ring on flux focusing heads, when the electromagnets are energized by the power means.

Another embodiment of the present invention involves a method of therapeutically placing an electromagnetic treatment Therapeutic Head in proximity of the head and cervical spine or other body areas to control cell death from stroke and other hypoxic injuries, comprising the steps of: assembling at least two groups of electromagnetic bodies having in each group at least two positive magnetic poles substantially in a single plane, having at least two negative magnetic poles substantially in a single plane, along with a flux return ring, flux focusing ring and focusing magnets; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body at a position facing the second containment body with the quadripolar, steep gradient field penetrating the body of the animal; and energizing the magnetic bodies with electric power so that each of the magnetic bodies generate a magnetic flux field.

An additional embodiment of the invention may involve a method of therapeutically placing an electromagnetic treatment device in proximity of the head and neck of an animal to control cell death from strokes and other hypoxic injuries of the nervous system, comprising the steps of: assembling at least two groups of electromagnetic bodies having at least, in each body, two positive magnetic poles substantially in a single plane, having at least two negative magnetic poles substantially in a single plane along with a flux return ring, focusing ring and focusing electromagnets attached to the focusing ring; orienting said two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing each said orientation of the plurality of magnetic bodies in a single containment body; selectively placing containment bodies at a position in relation to the head and neck to treat nervous tissue and to protect from cell death secondary to stroke or other hypoxic injuries; energizing the magnetic bodies with DC electric power so that each of the magnetic bodies generate a magnetic flux field.

G. Magnetic Treatment Device of the Invention for Control of Edema and Pain as well as Speeding Healing Rates Following Surgical Procedures and to Increase Healing of Chronic Non-Healing Wounds.

Reference will now be made in detail to the presently preferred embodiments of the invention, examples of which are illustrated in the accompanying drawings. Throughout the drawings, like reference characters are used to designate like elements.

One of the two electromagnetic heads and circuits of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration. Attached to the containment means are three (3) important and functional components of the technology. Flux return ring 16 is attached to the bottom of the described 4 electromagnetic heads, this ring enhances the flux field and controls unwanted stray flux from the opposite pole. A flux focusing ring 16 is positioned around the flux heads, it being about 2.5 inches wide (6.35 cm) and ¼ to ½ inches (6.3 5 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45°–90° angle to the long axis of the primary flux pole. In this position, the flux focusing coils along with the focusing ring will make the gradient steeper and increase the effective field strength. The flux return ring and the flux focusing ring are grounded to reduce stray, induction currents and the variables that they add to the therapeutic magnetic field.

As embodied herein, magnetic flux generator 12 comprises four substantially identical electromagnetic bodies on a containment means. Containment means may comprise a mounting board, a flux return ring 16a (made of a ferroconductor), a casing or any other structure that will hold electromagnetic bodies 18, 20, 22 and 24 in the desired configuration. A flux field focusing ring 16 is attached to the outer surface of the coils 18, 20, 22 and 24; this focusing ring holds focusing electromagnetic poles 18a, 20a, 22a and 24a. The structure must then be held in place for proper alignment of the attracting fields of the two heads of the invention as shown in FIG. 11. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 with their flux return ring and focusing ring along with the focusing magnets comprise electromagnetic heads as best shown in FIGS. 2, 3 and 11.

Each electromagnetic head includes a conducting wire 26 wound around a cast iron core 28. Wire 26 may be comprised of any conducting material, as for example, copper or aluminum. For example, FIG. 3 shows a suitable electromagnet made using a five inch (12.7 cm) outer diameter wire coil with a two inch (5.08 cm) center iron core 28 and a two inch (5.08 cm) coil space with 3200 turns of #22 copper wire. As shown in FIGS. 2 and 3, coils 19, 21, 23 and 25 of electromagnetic heads (shown in cut away) 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. FIG. 3 represents a cut away view with insulation 29 being cut away to reveal wire coil 26.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Electromagnetic focusing magnets 18a, 20a, 22a and 24a may be on separate rheostats to better balance the field. Rheostat 50 is preferable embodied as any conventional rheostat having a 50 amp 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head, may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

According to the invention, the therapeutic electromagnetic treatment device of the invention may be mounted on a support structure adapted to align the four electromagnets such that they may be aligned with the other head such that the heads are facing each other with the center axis of each electromagnet meeting in the center with opposite poles facing. This configuration increases the peak power of each pole and makes the gradient steeper. The increased peak power and increased slope of the gradient both improve the biological effect. FIG. 11 shows the means to support the two heads and to fasten them together. The two heads are magnetic flux generators. Flux generator 12 is preferably powered by a power source (not shown) like that described above. The flux generators 12 move in the x, y and z axis in order to get appropriate peak magnetic flux and peak magnetic gradient. Flux generators 12 may be moved manually or by a power driven actuating mechanism 54 such that flux generators 12 may be aligned with the desired position of a human or animal head or spine or any other portion of the body to which magnetic flux is to be applied. A magnetic flux field is generated by each of the electromagnetic poles on flux generator 12 when the electromagnetic poles are energized. A magnetic flux field so generated by the electromagnetic heads extends laterally from a planar surface such that magnetic flux impinges upon an area of the head and/or upper cervical spine or other parts of the body positioned between the two flux generators 12.

The support means 56 allows both the left and right side sections to be rolled into place forward and locked together by lock bars 52 and 53. Lock bar 53 is underneath the bed. Support means 56 contains the DC power source 14 and provides support for the quadripolar flux generators 12. The support means 56 also contains control meters 58, pole selectors 60 and voltage regulator (DC) 61. A lead counter weight 62 functions to counter balance the flux generators 12. The caster rollers 63 provide the ability to move support means 56 to the bedside.

The patient is placed in the static quadripolar field between the two flux generators 12. Alternately, one head may be used and manipulated such that the area of operative manipulation or poorly healing wound is properly treated by the double or single magnetic flux head of the invention.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the two flux generator heads are supported by support means such that the planar surface faces poles of each face in the attracting mode when two flux heads are energized.

Further, the four magnetic poles of each flux generator of the therapeutic electromagnetic treatment device may include two positive poles defining opposite diagonal vertices and said two negative poles defining opposite diagonal vertices of the quadrilateral shape, each of the magnetic poles being oppositely charged poles and being magnetically repelled by said like charged pole. A flux return ring is attached to the bottom of the described 4 electromagnetic heads, this ring enhances the flux field and controls unwanted stray electrical flux from the opposite pole. Further, a flux focusing ring is positioned around the flux heads, and an attachment means may hold the focusing ring in proper location for maximum benefit. Also attached to the flux focusing ring may be are focusing coils. These focusing electromagnetic coils may be attached to the flux focusing ring adjacent to the flux head of like charge and at a 45° to 90° angle to the long axis of the primary flux pole. In this position the flux focusing coils along with the focusing ring generates a steeper field gradient and increases the effective field strength. The flux return ring and the flux focusing ring may be grounded to reduce the stray induction currents and the variables that they add to the therapeutic magnetic field. The 4 electromagnetic poles, with flux return ring, focusing ring and focusing coils may be referred to as the "Therapeutic Head."

In another embodiment of the present invention, the plurality of electromagnetic bodies of the therapeutic electromagnetic treatment device may comprise four substantially identical electromagnet flux heads, two of the electromagnets having a positive magnetic pole in the substantially single plane and two of the electromagnets having a negative magnetic pole in the substantially single plane, each of the four electromagnets generating a magnetic flux field when energized by the power means. The four electromagnets may each also comprise a cast iron core wound with electrically conducting wire, which wire may be, inter alia, a copper or aluminum wire.

Additionally, the quadrilateral shape of the therapeutic electromagnetic treatment device may be, inter alia, a parallelogram shape, a rectangle shape, or a square shape.

The power means may also comprise a direct current generator and be electrically connected to each of the four electromagnets of a single flux generator head along with connection to the flux focusing magnets. There may also be a power control means for controlling the amount of electrical power supplied to each of the four electromagnets so as to regulate the magnetic flux field generated by each of the four electromagnets in both magnetic flux generator heads.

In another embodiment of the present invention, the containment means may be mounted on a support structure adapted to align said four electromagnets of the magnetic flux generator head in the same orientation as the second magnetic flux generator head such that the two heads are facing and in a parallel position. The support structure may also comprise a cabinet for the support of each magnetic flux generator head, the support structure being mounted on coasters for easy mobility and having means to fasten the two flux generator heads together once they are in position over the bed or table, the bed being for supporting the body of a living animal in which the body area of interest is placed between the two flux generator heads, the magnetic flux field generated by each of the four electromagnets of each flux generator head exposes the human or animal body area to 50 up to 500 milli Tesla of energy and steep three dimensional field gradients which can be manipulated by the flux return ring, flux focusing ring on flux focusing heads, when said electromagnets are energized by said power means.

Another embodiment of the present invention involves a method of therapeutically placing an electromagnetic treatment Therapeutic Head in proximity of the body areas to be treated, comprising the steps of: assembling at least two groups of electromagnetic bodies having in each group at least two positive magnetic poles substantially in a single plane, having at least two negative magnetic poles substantially in a single plane, along with a flux return ring, flux focusing ring and focusing magnets; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing the orientation of the plurality of magnetic bodies in a single containment body; selectively placing the containment body at a position facing the second containment body with the quadripolar, steep gradient field penetrating the body of the animal; and energizing the magnetic bodies with electric power so that each of the magnetic bodies generate a magnetic flux field.

Additionally, an embodiment of the instant invention may include a method of therapeutically placing an electromagnetic treatment device in proximity of the animal body part to be treated, comprising the steps of: assembling at least two groups of electromagnetic bodies having at least, in each body, two positive magnetic poles substantially in a single plane, having at least two negative magnetic poles substantially in a single plane along with a flux return ring, focusing ring and focusing electromagnets attached to the focusing ring; orienting the two positive poles and the two negative poles of said plurality of magnetic bodies in a single plane to define the four vertices of a rectangle shape with the two positive poles defining opposite diagonal vertices and the two negative poles defining opposite vertices of the rectangular shape; fixing each orientation of the plurality of magnetic bodies in a single containment body; selectively placing containment bodies at a position in relation to the body part to treat the area of acute surgical procedures to control pain, swelling and to promote healing; similar treatment would be applied to chronic non-healing wounds to bring about healing; energizing said magnetic bodies with DC electric power so that each of the magnetic bodies generate a magnetic flux field.

H. Magnetic Treatment Device of this Invention for the Control of Pain and Sludging of Sickled Cells in Sickle Cell Disease (SMS-SC).

Reference will now be made in detail to the presently preferred embodiments of the invention, examples of which are illustrated in the accompanying drawings. Throughout the drawings, like reference characters are used to designate like elements.

One of the two electromagnetic heads and circuits of the invention is schematically illustrated in FIG. 1. Treatment device 10 includes a magnetic flux generator 12 and a power source 14. According to the invention, magnetic flux generator 12 comprises a plurality of electromagnetic bodies having at least four magnetic poles substantially in a single plane, the magnetic poles being oriented to define the four vertices of a quadrilateral shape. Preferably, the four magnetic poles comprise two positive and two negative poles, the two positive poles defining opposite diagonal vertices and the two negative poles defining opposite shape. Each of the magnetic poles are magnetically attracted to the two oppositely charged poles and magnetically repelled by the like charged poles. Containment means hold the magnetic poles of the magnetic bodies in the above described configuration. Attached to the containment means are three (3) important and functional components of the technology. Flux return ring 16 is attached to the bottom of the described 4 electromagnetic heads, this ring enhances the flux field and controls unwanted stray flux from the opposite pole. A flux focusing ring 16 is positioned around the flux heads, it being about 2.5 inches wide (6.35 cm) and ¼ to ½ inches (6.3 5 mm–12.7 mm) thick. Attachment means hold the focusing ring in proper location for maximum benefit. Attached to the flux focusing ring are focusing coils 18a, 20a, 22a and 24a. These focusing coils are attached to the flux focusing ring in proximity to a head of like charge and at a 45°–90° angle to the long axis of the primary flux pole. In this position, the flux focusing coils along with the focusing ring will make the gradient steeper and increase the effective field strength. The flux return ring and the flux focusing ring are grounded to reduce stray, induction currents and the variables that they add to the therapeutic magnetic field.

As embodied herein, magnetic flux generator 12 comprises four substantially identical electromagnetic bodies on a containment means. Containment means may comprise a mounting board, a flux return ring 16a (made of a ferroconductor), a casing or any other structure that will hold electromagnetic bodies 18, 20, 22 and 24 in the desired configuration. A flux field focusing ring 16 is attached to the outer surface of the coils 18, 20, 22 and 24; this focusing ring holds focusing electromagnetic poles 18a, 20a, 22a and 24a. The structure must then be held in place for proper alignment of the attracting fields of the two heads of the invention as shown in FIG. 11. In the preferred embodiment, electromagnetic bodies 18 and 22 each form a negative magnetic pole while electromagnetic bodies 20 and 24 each form a positive magnetic pole. The positive and negative magnetic poles of magnetic bodies 18, 20, 22 and 24 are aligned in substantially a single plane and are oriented in a quadrilateral configuration with positive poles oriented diagonally opposite one another and negative poles oriented diagonally opposite one another. Electromagnetic bodies 18, 20, 22 and 24 with their flux return ring and focusing ring along with the focusing magnets comprise electromagnetic heads as best shown in FIGS. 2, 3 and 11.

Each electromagnetic head includes a conducting wire 26 wound around a cast iron core 28. Wire 26 may be comprised of any conducting material, as for example, copper or aluminum. For example, FIG. 3 shows a suitable electromagnet made using a five inch (12.7 cm) outer diameter wire coil with a two inch (5.08 cm) center iron core 28 and a two inch (5.08 cm) coil space with 3200 turns of #22 copper wire. As shown in FIGS. 2 and 3, coils 19, 21, 23 and 25 of electromagnetic heads (shown in cut away) 18, 20, 22 and 24, respectively, are each connected to a power source by wires 30 and 32. The conducting wire 26 is wound around a porous cast iron core (or laminated steel) 28 in such a fashion as to center the magnetic flux in the geometric center of the iron core. Current flow in an electric conductor emits magnetic flux at right angles to the flow of current. Therefore, the flux is centered in the core. Accordingly, it is preferred that the core is circular. FIG. 3 represents a cut away view with insulation 29 being cut away to reveal wire coil 26.

According to the invention, power means for magnetically energizing the electromagnetic bodies is provided so that energized electromagnetic bodies can each generate a magnetic flux field. As embodied herein, a power source 14 includes a control unit 34, a direct current generator 36 and an alternating current power source 38. Direct current generator 36 is preferably a bridge rectifier and a series of filters. It is preferable that the alternating current power source 38 be a 120 volt AC source. It is preferred that the direct current generator 36 be capable of producing a 30 amp, 120 volt DC current. Control unit 34 includes an on-off power switch 40 for controlling the flow of direct electric current (battery grade) to magnetic flux generator 12. Control unit 34 also includes a volt meter 42 and an amp meter 44 for monitoring of the power and current supplied to magnetic flux generator 12 by direct current generator 36. Fuses 46 and 48 protect magnetic flux generator 12 against power surges. Fuses 46 and 48 may, for example, be 30 amp electric fuses. A rheostat 50 permits regulation of the direct current being supplied to magnetic flux generator 12 at any given time. Electromagnetic focusing magnets 18a, 20a, 22a and 24a may be on separate rheostats to better balance the field. Rheostat 50 is preferable embodied as any conventional rheostat having a 50 amp 120 volt capacity. As shown in FIGS. 1 and 2, each of the magnetic heads 18, 20, 22 and 24 may be electrically connected with power controller 34 by a single pair of wires 30 and 32. Preferably, each of the magnetic poles 18, 20, 22 and 24 making up the head, may be individually regulated such that symmetric magnetic power may be balanced among all heads. It is anticipated that each magnetic treatment head could alternatively be individually connected to one of four rheostats in control unit 34 such that electric current supplied to each of the individual treatment heads could be individually regulated.

Electromagnetic coils 19 and 23 of electromagnetic heads 18 and 22, and electromagnetic coils 21 and 25 of electromagnetic heads 20 and 24 are preferably connected to the DC generator such that heads 18 and 22 generate magnetic flux fields opposite from the magnetic flux fields generated by heads 20 and 24. As can be seen in FIG. 2, coils 19 and 23 are connected to the DC power source so as to generate a negative magnetic field while coils 21 and 25 are oppositely connected to the DC power source so as to generate a positive magnetic field. In an alternative embodiment of the invention, electromagnetic coils 19, 21, 23 and 25 may be connected to the DC power source such that each generates a positive magnetic field, a negative magnetic field, or some combination thereof.

According to the invention, the therapeutic electromagnetic treatment device of the invention may be mounted on a support structure adapted to align the four electromagnets such that they may be aligned with the other head such that the heads are facing each other with the center axis of each electromagnet meeting in the center with opposite poles facing. This configuration increases the peak power of each pole and makes the gradient steeper. The increased peak power and increased slope of the gradient both improve the biological effect. FIG. 11 shown the means to support the two heads and to fasten them together. The two heads are magnetic flux generators. Flux generator 12 is preferably powered by a power source (not shown) like that described above. The flux generators 12 move in the x, y and z axis in order to get appropriate peak magnetic flux and peak magnetic gradient. Flux generators 12 may be moved manually or by a power driven actuating mechanism 54 such that flux generators 12 may be aligned with the desired position of a human or animal head or spine or any other portion of the body to which magnetic flux is to be applied. A magnetic flux field is generated by each of the electromagnetic poles on flux generator 12 when the electromagnetic poles are energized. A magnetic flux field so generated by the electromagnetic heads extends laterally from a planar surface such that magnetic flux impinges upon an area of the head and/or upper cervical spine or other parts of the body positioned between the two flux generators 12. FIG. 6 is another embodiment of the technology for sickle cell crisis which involves large areas of the body.

The support means 56 allows both the left and right side sections to be rolled into place forward and locked together by lock bars 52 and 53. Lock bar 53 is underneath the bed. Support means 56 contains the DC power source 14 and provides support for the quadripolar flux generators 12. The support means 56 also contains control meters 58, pole selectors 60 and voltage regulator (DC) 61. A lead counter weight 62 functions to counter balance the flux generators 12. The caster rollers 63 provide the ability to move support means 56 to the bedside.

The patient is placed in the static quadripolar field between the two flux generators 12. Alternately, one head may be used and manipulated such that the area of operative manipulation or poorly healing wound is properly treated by the double or single magnetic flux head of the invention.

In a preferred embodiment, a therapeutic electromagnetic treatment device adapted for placement against the bodies of living animals comprises: a plurality of electromagnetic bodies having at least four magnetic poles substantially in a single plane, the magnetic poles being oriented to define the four vertices of a quadrilateral shape, each of the magnetic poles exerting a magnetic force on the other three poles when the poles are electrically charged; containment of a ferroconductor flux return ring bolted to the end of the pole which is turned away from the animal or human along with a ferromagnetic focusing ring which contains a ferroconductor metal ring and a electromagnet of the same polarity as the pole attached to the focusing ring in proximity to the four poles of the quadrilateral shape; containment means for holding the magnetic poles of the magnetic bodies in the orientation; and power means for magnetically energizing the electromagnetic bodies, the energized electromagnetic bodies each generating a magnetic flux field; further, the four magnetic poles when energized together generate flux field with a sharp three dimensional gradient and comprises a flux generator head.

A further embodiment comprises the therapeutic electromagnetic treatment device described above further wherein the two flux generator heads are supported by support means such that the planar surface faces poles of each face in the attracting mode when two flux heads are energized.

In another embodiment of the invention, the four magnetic poles of each flux generator include two positive poles defining opposite diagonal vertices and the two negative poles defining opposite diagonal vertices of the quadrilateral shape, each of the magnetic poles being oppositely charged poles and being magnetically repelled by the like charged pole. A flux return ring may be attached to the bottom of the described 4 electromagnetic heads, this ring enhances the flux field and controls unwanted stray electrical flux from the opposite pole. A flux focusing ring may be positioned around the flux heads. Also, an attachment means may hold the focusing ring in proper location for maximum benefit. Also attached to the flux focusing ring may be focusing coils. These focusing electromagnetic coils are attached to the flux focusing ring adjacent to the flux head of like charge and at a 45° to 90° angle to the long axis of the primary flux pole. In this position the flux focusing coils along with the focusing ring generates a steeper field gradient and increases the effective field strength. The flux return ring and the flux focusing ring may be grounded to reduce the stray induction currents and the variables that they add to the therapeutic magnetic field. The 4 electromagnetic poles, with flux return ring, focusing ring and focusing coils may be referred to as the "Therapeutic Head."

In another embodiment, the plurality of electromagnetic bodies of the therapeutic electromagnetic treatment device may comprise four substantially identical electromagnet flux heads, two of the electromagnets having a positive magnetic pole in the substantially single plane and two of the electromagnets having a negative magnetic pole in the substantially single plane, each of the four electromagnets generating a magnetic flux field when energized by the power means.

Further, the four electromagnets may each comprise a cast iron core wound with electrically conducting wire which may be, inter alia, a copper or aluminum wire.

The quadrilateral shape of the therapeutic electromagnetic treatment device may also be, inter alia, a parallelogram shape, a rectangle shape, or a square shape.

The power means of the therapeutic electromagnetic treatment device may comprise a direct current generator and be electrically connected to each of the four electromagnets of a single flux generator head along with connection to the flux focusing magnets. The therapeutic electromagnetic treatment device may comprise a power control means for controlling the amount of electrical power supplied to each of the four electromagnets so as to regulate the magnetic flux field generated by each of the four electromagnets in both magnetic flux generator heads.

Also, the containment means of the therapeutic electromagnetic treatment device may be mounted on a support structure adapted to align said four electromagnets of the magnetic flux generator head in the same orientation as the second magnetic flux generator head such that the two head are facing and in a parallel position. The support structure may comprise a cabinet for the support of each magnetic flux generator head, the support structure being mounted on coasters for easy mobility and has means to fasten the two flux generator heads together once they are in position over the bed or table, the bed being for supporting the body of a living animal in which the head and cervical area is placed between the two flux generator heads, the magnetic flux field generated by each of said four electromagnets of each flux generator head exposes the human or animal body area to 50 up to 500 milli Tesla of energy and steep three dimensional field gradients which can be manipulated by the flux return ring, flux focusing ring on flux focusing heads, when said electromagnets are energized by said power means.

Another embodiment of the present invention involves a method of therapeutically placing an electromagnetic treatment Therapeutic Head in proximity of the animal or human body areas which are involved in the sickling of cells, comprising the steps of: assembling at least two groups of electromagnetic bodies having in each group at least two positive magnetic poles substantially in a single plane, having at least two negative magnetic poles substantially in a single plane, along with a flux return ring, flux focusing ring and focusing magnets; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing said orientation of the plurality of magnetic bodies in a single containment body; selectively placing the containment body at a position facing the second containment body with the quadripolar, steep gradient field penetrating the body of the animal; and energizing the magnetic bodies with electric power so that each of said magnetic bodies generate a magnetic flux field.

An embodiment of the present invention may also include a method of therapeutically placing an electromagnetic treatment device in proximity of the body of a human having a sickle cell crisis with sickling of cells, pain and sludging, comprising: assembling at least two groups of electromagnetic bodies having at least, in each body, two positive magnetic poles substantially in a single plane, having at least two negative magnetic poles substantially in a single plane along with a flux return ring, focusing ring and focusing electromagnets attached to the focusing ring; orienting the two positive poles and the two negative poles of the plurality of magnetic bodies in a single plane to define the four vertices of a rectangle shape with the two positive poles defining opposite diagonal vertices and the two negative poles defining opposite vertices of the rectangular shape; fixing each orientation of the plurality of magnetic bodies in a single containment body; selectively placing containment bodies at a position in relation to the body part to be treated such that the steep three dimensional field gradient blocks red blood cell sickling and sludging as it controls pain of the sickling crisis; energizing the magnetic bodies with DC electric power so that each of the magnetic bodies generates a magnetic flux field.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A therapeutic electromagnetic treatment device adapted to interact with bodies of living organisms, comprising:

a plurality of electromagnetic bodies comprising a plurality of magnetic poles substantially in a single plane; said magnetic bodies being oriented to define the four vertices of a quadrilateral shape, and each of said magnetic poles exerting a magnetic force on the other plurality of magnetic poles when said poles are electrically charged; a ferroconductor flux return ring secured to at least one of the magnetic poles;

a ferromagnetic focusing ring containing a ferroconductor metal ring and a electromagnet of the same polarity as the pole attached to the focusing ring in proximity to the four poles of the quadrilateral shape; containment means for holding said magnetic poles of said magnetic bodies in said orientation; and power supply for magnetically energizing said electromagnetic bodies, said energized electromagnetic bodies, each generating a magnetic flux field, said four magnetic poles when energized together generate flux field with a sharp three dimensional gradient; and said ferroconductor flux return ring increasing the strength and radiant without altering the centered charge and symmetry of the three dimensional steep gradient magnetic flux field.

2. The therapeutic electromagnetic treatment device of claim 1, wherein said four magnetic poles include two positive and two negative poles, said two positive poles defining opposite diagonal vertices and said two negative poles defining opposite diagonal vertices of the quadrilateral shape, each of said magnetic poles being magnetically attracted by said two oppositely charged poles and being magnetically repelled by said like charged pole.

3. The therapeutic electromagnetic treatment device of claim 1, wherein said plurality of electromagnetic bodies comprise four substantially identical electromagnets, two of said electromagnets having a positive magnetic pole in said substantially single plane and two of said electromagnets having a negative magnetic pole in said substantially single plane, each of said four electromagnets generating a magnetic flux field when energized by said power means.

4. The therapeutic electromagnetic treatment device of claim 3 wherein said four electromagnets each comprise a cast iron core wound with electrically conducting wire.

5. The therapeutic electromagnetic treatment device of claim 4 wherein said electrically conducting wire comprises wire selected from the group consisting of copper wire and aluminum wire.

6. The therapeutic electromagnetic treatment device of claim 3 wherein the shape of said quadrilateral shape is selected from the group consisting of a parallelogram, a rectangle, and a square shape.

7. The therapeutic electromagnetic treatment device of claim 1 wherein said power supply comprises direct current generator and is electrically connected to each of said four electromagnets.

8. The therapeutic electromagnetic treatment device of claim 1 further comprising power control means for controlling the amount of electrical power supplied to each of said four electromagnets so as to regulate the magnetic flux field generated by each of said four electromagnets.

9. The therapeutic electromagnetic treatment device of claim 1 wherein said containment means is mounted on a support structure adapted to align said four electromagnets against the body of a living animal.

10. The therapeutic electromagnetic treatment device of claim 9 wherein said support structure comprises an elongated planar table having a first planar surface, said first planar surface of said table adapted for supporting the body of a living animal against which said four electromagnets are placed, said containment means being movably attached to said planar table for movable alignment with select portions of the living animal body, the magnetic flux field generated by each of said four electromagnets extending above said first planar surface of said table when said four electromagnets are energized by said power means.

11. The therapeutic electromagnetic treatment device of claim 10 wherein said planar table has a cavity in which said containment means being movably mounted on said second planar surface.

12. The therapeutic electromagnetic treatment device of claim 9 wherein said support structure comprises a chair having a substantially horizontal seating surface and a substantially vertical back support surface, said seating and back support surfaces adapted for supporting the body of a living animal against which said four electromagnets are placed, said containment means being movably attached to said chair for movable alignment with select portions of the living animal body, the magnetic flux field generated by each of said four electromagnets extending out from the substantially vertical back support surface when said electromagnets are energized by said power means.

13. The therapeutic electromagnetic treatment device of claim 12 wherein said chair has a vertically extending cavity behind said vertical back support surface and said containment means is mounted for vertical movement within said cavity.

14. The therapeutic electromagnetic treatment device of claim 1 further comprising electrically powered means for moving said containment means vertically and horizontally within said vertically extending cavity.

15. A method of therapeutically treating a living organism with an electromagnetic treatment device, comprising the steps of:
assembling at least one group of electromagnetic bodies having at least two positive magnetic poles substantially in a single plane, having at least two negative magnetic poles substantially in a single plane;
providing at least a ferroconductive flux return ring on each of the magnetic poles:
orienting said two positive poles and said two negative poles of said plurality of magnetic bodies in a single plane to define the four vertices of a rectangle shape with said two positive poles defining opposite diagonal vertices of said two negative poles defining opposite vertices of the rectangular shape;
fixing said orientation of said plurality of magnetic bodies in a single containment body;
selectively placing said containment body at a position against the organism or a selected area to be treated; and
energizing said magnetic bodies with electric power so that each of said magnetic bodies generate a magnetic flux field within said selected area; and
said ferroconductive flux return ring increasing the strength and radiant without altering the centered charge and symmetry of the three dimensional steep gradient magnetic flux field.

16. The method in claim 15, wherein the organism to be treated is a human being.

17. The method in claim 15, further comprising the step of positioning the containment body over the area of a human body producing pain sensations in order to improve blood circulation in the human body.

18. The method in claim 15, further comprising the step of placing the containment body facing the chest of the human body and exposing the myocardium to a steep field gradient penetrating the heart of the human body, for controlling pathological processes which accompany a myocardial infarction such as arrhythmia, chest pain and decreased myocardial blood flow in the human body.

19. The method in claim 15, wherein said containment body placed in relation to the heart of a human to treat said myocardial infarction controls the pathophysiology of the heart undergoing a myocardial infarction.

20. The method in claim 15, wherein said containment means is placed at a position in relation to the head and neck for treating seizures, cerebral edema and upper cervical cord edema.

21. The method in claim 15, wherein the containment body is positioned in a bank of magnetic flux generator heads for exposing the body to a steep field gradient penetrating the body of the human being treated for controlling pathological processes which accompany a serious burn.

22. The method in claim 15, wherein said containment bodies positioned in relation to the body of the human for treating the complication of severe burns controls the pathophysiology of severe burns.

23. The method in claim 15, wherein the containment body is positioned facing a second containment body with a quadripolar, steep gradient field penetrating the body of the animal for potentiating the effects of pharmaceuticals.

24. The method in claim 23, wherein said containment bodies position facing said second containment body with the quadripolar, steep gradient field penetrating the body of the animal to control cell death from stroke and other hypoxic injuries.

25. The method in claim 15, wherein said containment body is positioned in relation to the head and neck to treat nervous tissue and to protect from cell death secondary to stroke or other hypoxic injuries.

26. A method of therapeutically placing an electromagnetic treatment therapeutic head in proximity of the body areas to be treated, comprising the steps of:
assembling at least two groups of electromagnetic bodies having in each group at least two positive magnetic poles substantially in a single plane, having at least two negative magnetic poles substantially in a single plane, along with a ferroconductive flux return ring, flux focusing ring and focusing magnets;
orienting said two positive poles and said two negative poles in a single plane to define the four vertices of a rectangle shape with said two positive poles defining opposite diagonal vertices and said two negative poles defining opposite vertices of the rectangular shape;
fixing said orientation of said of magnetic bodies in a single containment body;
selectively placing said containment body at a position facing a second containment body with the quadripolar, steep gradient field penetrating the body of the animal; and
energizing said magnetic bodies with electric power so that each of said magnetic bodies generate a magnetic flux field;
said ferroconductive flux ring returning the magnetic flux for increasing the strength and gradient without altering the centered charge and symmetry of the three dimensional gradient magnetic flux field.

27. A method of therapeutically placing an electromagnetic treatment device in proximity of the animal body part to be treated, comprising the steps of:
assembling at least two groups of electromagnetic bodies having at least, in each body, two positive magnetic poles substantially in a single plane, having at least two negative magnetic poles substantially in a single plane, along with a ferroconductive flux return ring, focusing ring, and focusing electromagnets attached to the focusing ring;

orienting said two positive poles and said two negative poles of said magnetic bodies in a single plane to define the four vertices of a rectangle shape with said two positive poles defining opposite diagonal vertices and said two negative poles defining opposite vertices of the rectangular shape;

fixing each said orientation of said magnetic bodies in a single containment body; and selectively placing containment bodies at a position in relation to a body part to be treated, energizing said magnetic bodies with DC electric power so that each of said magnetic bodies generate a magnetic flux field;

said ferroconductive flux ring returning the magnetic flux for increasing the strength and gradient without altering the centered charge and symmetry of the three dimensional gradient magnetic flux field.

28. The method of claim 27 wherein the body part to be treated is selected from the group consisting of an area of acute surgical procedures, to control pain and swelling and to promote healing, and an area of chronic non-healing wounds, to bring about healing.

29. The method in claim 27, wherein the method is utilized for treating the sickling of human cells, and said containment body would be positioned facing the second containment body with the quadripolar, steep gradient field penetrating the body of the animal.

30. The method in claim 27, wherein said containment body is positioned in relation to the body part to be treated such that the steep, three dimensional field gradient blocks, red blood cells, sickling and sludging as it controls pain of a sickling crisis.

* * * * *